United States Patent
Trees et al.

(10) Patent No.: US 11,422,919 B2
(45) Date of Patent: Aug. 23, 2022

(54) SYSTEMS AND METHODS FOR SCIENTIFIC EVALUATION OF PROGRAM CODE OUTPUTS

(71) Applicant: Akili Interactive Labs, Inc., Boston, MA (US)

(72) Inventors: Jason Trees, Dedham, MA (US); Titiimaea Alailima, Cambridge, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 0 days.

(21) Appl. No.: 16/748,688

(22) Filed: Jan. 21, 2020

(65) Prior Publication Data

US 2021/0224180 A1 Jul. 22, 2021

(51) Int. Cl.
- *G16H 10/20* (2018.01)
- *G06F 11/36* (2006.01)
- *G06F 11/34* (2006.01)
- *G06F 17/18* (2006.01)

(52) U.S. Cl.
CPC ...... *G06F 11/3616* (2013.01); *G06F 11/3466* (2013.01); *G06F 11/3612* (2013.01); *G06F 17/18* (2013.01); *G16H 10/20* (2018.01)

(58) Field of Classification Search
CPC .......................... G16H 10/20; G06F 11/3616
See application file for complete search history.

(56) References Cited

U.S. PATENT DOCUMENTS

| | | | |
|---|---|---|---|
| 9,740,831 B2 | 8/2017 | Burns et al. | |
| 9,996,678 B2 | 6/2018 | Johnson | |
| 10,049,772 B1* | 8/2018 | Price, Jr | G16H 70/60 |
| 2011/0313782 A1 | 12/2011 | DeMeyer et al. | |

(Continued)

FOREIGN PATENT DOCUMENTS

| | | | |
|---|---|---|---|
| CN | 101702137 A * | 5/2010 | |
| WO | 2019035910 A1 | 2/2019 | |

OTHER PUBLICATIONS

E. S. Mesh, G. Burns and J. S. Hawker, "Leveraging Expertise to Support Scientific Software Process Improvement Decisions," in Computing in Science & Engineering, vol. 16, No. 3, pp. 28-34, May-Jun. 2014, doi: 10.1109/MCSE.2014.10. (Year: 2014).*

(Continued)

*Primary Examiner* — Sheetal R Paulson
(74) *Attorney, Agent, or Firm* — Gregory Finch; Finch Paolino, LLC

(57) ABSTRACT

Systems and methods for distributed scientific evaluation of software product comprising a digital health intervention or software as a medical device product. In certain embodiments, a scientific evaluation system is operably configured to analyze one or more safety, efficacy, performance, and/or quality assurance aspects for program code outputs of the software product. In further embodiments, a scientific evaluation system is operably configured to configure and administer a distributed scientific evaluation, research study and/or clinical trial for the software product. In certain embodiments, a scientific evaluation system is configured to enable scientific evaluation of one or more program code outputs of a software product for one or more indication or intended use.

10 Claims, 16 Drawing Sheets

(56) References Cited

U.S. PATENT DOCUMENTS

2018/0121856 A1    5/2018  Song et al.
2019/0206519 A1    7/2019  Eteminan et al.

OTHER PUBLICATIONS

A. Yagü, J. Garbajosa, J. Pérez and J. Díaz, "Analyzing Software Product Innovation Assessment by Using a Systematic Literature Review," 2014 47th Hawaii International Conference on System Sciences, 2014, pp. 5049-5058, doi: 10.1109/HICSS.2014.620. (Year: 2014).*
International Search Report, International application No. PCT/US2021/014364, dated Dec. 28, 2017 ISA/US, Alexandria, VA.
Written Opinion of the International Searching Authority, International application No. PCT/US2021/014364, dated Apr. 20, 2021. ISA/US, Alexandria, VA.

* cited by examiner

SYSTEMS AND METHODS FOR SCIENTIFIC EVALUATION OF PROGRAM CODE OUTPUTS

FIELD

The present disclosure relates to the field of software quality assurance systems; in particular, systems and methods for scientific evaluation and data-driven analysis of program code outputs for digital health interventions and software as a medical device products.

BACKGROUND

Before a new medical treatment (e.g., pharmaceuticals) or device (e.g., surgical instruments or implants) may be dispensed to the public, the relevant regulatory agency for the jurisdiction in which market approval for the treatment or device is being sought, e.g. United States Food and Drug Administration (FDA) in the United States, requires that the manufacturers of the pharmaceuticals, devices, instruments, or implants conduct extensive clinical trial research in order to demonstrate the clinical effectiveness, safety, and medical advantage of their products. Extensive and often complex clinical trial protocols are developed that define, for example, targeted demographics, proposed medications, patient regimens, forms for collection, types of statistically relevant data, the timing or order of events within the study, often even the layout of the reporting data, or other suitable data.

An expanding area of medical devices and technologies is in the area of digital health interventions (i.e. interventions delivered via digital technologies such as smartphones, website, text messaging) to provide effective, cost-effective, safe, and scalable interventions to improve health and healthcare. Digital health interventions (DHI) of software as a medical device (SaMD) can be used to promote healthy behaviors, improve outcomes in people with long term conditions such as cardiovascular disease, diabetes and mental health conditions and provide remote access to effective treatments; for example, computerized cognitive behavioral therapy for mental health and somatic problems. Software as a Medical Device (SaMD) is defined by the International Medical Device Regulators Forum (IMDRF) as "software intended to be used for one or more medical purposes that perform these purposes without being part of a hardware medical device." DHIs are often complex interventions with multiple components, and many have multiple aims including enabling users to be better informed about their health, share experiences with others in similar positions, change perceptions and cognitions around health, assess and monitor specified health states or health behaviors, titrate medication, clarify health priorities and reach treatment decisions congruent with these, and improve communication between patients and health care professionals (HCP). Active components may include information, psychoeducation, personal stories, formal decision aids, behavior change support, interactions with HCP and other patients, self-assessment or monitoring tools (questionnaires, wearables, monitors, and effective theory-based psychological interventions developed for face-to-face delivery such as cognitive behavioral therapy or mindfulness training).

Regulatory review and approval of DHIs and SaMD products incorporates unique regulatory evaluation considerations that are not relevant to "traditional" medical treatments and devices. Clinical evaluation of SaMD and DHIs may require manufacturers to continuously generate, collect, analyze, and assess the clinical data pertaining to a SaMD/DHI in order to generate clinical evidence to verify the clinical association and the performance metrics of the product when used as intended by the manufacturer. SaMD and DHIs may be further subject to on-going lifecycle scrutiny to thoroughly evaluate the product's performance. Once the product is on the market (post-market), as part of normal lifecycle management processes, the manufacturer may be required to continuously collect real-world performance data (e.g., complaints, safety data), to further understand the user's needs to ensure the product is meeting those needs, and to monitor the product's continued safety, effectiveness and performance in real-world use.

The unique nature of SaMD and DHI products as compared to "traditional" medical treatments and devices pose specific challenges with respect to clinical evaluation and clinical trials for such products. There exists a need for a systems and methods to support scientific evaluation and clinical trials of SaMD and DHI products. Through applied effort, ingenuity, and innovation, Applicant has identified deficiencies of prior art solutions and has developed a solution that is embodied by the present disclosure, which is described in detail below.

SUMMARY

In order to provide a basic understanding of the invention, the following is a simplified summary of certain embodiments thereof. This summary is not an extensive and is not intended to identify key/critical elements of the invention or to delineate the scope of the invention. Its sole purpose is to present embodiments of the invention in a simplified form as a prelude to the more detailed description that is further below.

An object of the present disclosure includes systems, methods, devices and computer-readable media configured to collect, process, and manage data from one or more endpoints, across one or more platforms or systems, associated with a DHI/SaMD program, product or platform. Further objects provide for methods for quality control, quality analysis, and quality assurance of program code as well as feature set validation of DHI/SaMD products.

An object of the present disclosure includes systems, methods, devices and computer-readable media configured to process and analyze data being generated through one or more user interactions with a DHI and/or a SaMD program, product or platform for the purpose of providing a statistical analysis of a clinical association between the output of a DHI/SaMD and a targeted clinical condition (to include a pathological process or state); and that the DHI and/or SaMD provides the expected technical and clinical data as defined by manufacturer specifications.

An object of the present disclosure includes a data management system to assess safety, efficacy, performance, and/or patient outcomes associated with a DHI and/or SaMD program, product or platform; and to provide for a distributed platform to generate an accumulating knowledge base associated with a DHI/SaMD that can be used to guide decision-making for manufacturers of DHIs/SaMDs.

An object of the present disclosure includes a data management system and distributed platform for research and evaluation of a DHI/SaMD. Certain embodiments of the data management system and distributed platform may be configured to assess patient outcomes and overall impact of a DHI/SaMD across a patient population and provide data-driven analysis to improve human-centered design methods.

An object of the present disclosure includes a data processing and data management system for development, analysis and/or validation of causal models related to one or more components of a DHI/SaMD. In accordance with some embodiments, a data processing and management system is configured to identify one or more essential or active components of a DHI/SaMD (and its delivery package). Certain embodiments may be configured to process and analyze data according to certain predefined business logic or rules-based framework(s); such as, for example, a Multiphase Optimization Strategy (MOST). Certain embodiments may be configured to process and analyze data according to one or more predictive model and/or machine learning framework(s), including but not limited to linear/logistic regression, principal component analysis, a generalized linear mixed model, a random decision forest, a support vector machine, and an artificial neural network.

An object of the present disclosure is to provide for systems and methods for conducting randomized controlled trials (RCTs) for DHIs/SaMDs. Certain embodiments provide for systems and methods for manufacturers of DHIs/SaMDs to generate more useful data through: improving methods of early formative product design and development; better understanding of when and how short-term proxy outcomes should be used and when definitive outcomes are needed; better methods for improving internal validity of trials and/or feature analysis without jeopardizing external validity; improved methods for enhancing DHI/SaMD uptake and minimizing missing data; and better methods for considering whether and how DHI/SaMD can become scalable and sustainable across a targeted patient population.

An object of the present disclosure is to provide for a distributed research and evaluation platform configured to enable more useful synthesis and comparison of data generated by different studies of DHIs and SaMDs through: improved specification and classification of context, target populations, digital health interventions and their components, using more appropriate comparators for the stage of the research process, and improved reporting of trials and studies of DHIs and SaMDs.

Certain aspects of the present disclosure provide for a computer-implemented system comprising at least one server being communicably engaged with a communications network to receive a plurality of input data from one or more endpoints, the one or more endpoints comprising one or more electronic devices being associated with at least one user in a user population, the plurality of input data comprising a plurality of user-generated inputs in response to one or more computerized stimuli or interactions, the one or more computerized stimuli or interactions being associated with a targeted medical or personal wellness output; wherein the at least one server comprises a processor, a database and a non-transitory computer-readable medium having one or more instructions stored thereon that, when executed, cause the processor to perform one or more operations, the one or more instructions comprising instructions for analyzing, for the at least one user in the user population, a stimulus-response pattern between the one or more computerized stimuli or interactions and the plurality of user-generated inputs at two or more time points to determine one or more performance metrics for the at least one user in the user population; analyzing the plurality of input data and the one or more performance metrics to determine one or more outcome metrics for the at least one user in the user population; analyzing, according to a validation model, the one or more computerized stimuli or interactions and the one or more user outcome metrics to determine one or more efficacy metrics associated with the targeted medical or personal wellness output; and outputting the one or more user outcome metrics and the one or more efficacy metrics to one or more administrator devices.

In accordance with certain embodiments, the one or more instructions may further comprise instructions for segmenting the user population into two or more user groups according to one or more scientific evaluation parameters and/or protocols. The one or more computerized stimuli or interactions may comprise an instance of a mobile software application executing on a mobile electronic device, wherein the mobile software application may comprise a computer-implemented therapy or intervention associated with a targeted physiological or cognitive condition or state.

In accordance with certain embodiments, the one or more instructions may further comprise instructions for modifying or configuring the one or more computerized stimuli or interactions according to one or more scientific evaluation parameters and/or protocols. The one or more instructions may further comprise instructions for continuously receiving the plurality of input data from the one or more electronic devices and segmenting the plurality of input data according to one or more scientific evaluation parameters and/or protocols. In accordance with certain embodiments, the one or more instructions may further comprise instructions for modifying one or more user permission or revoking user access to the mobile software application according to one or more scientific evaluation parameters and/or protocols.

In accordance with further embodiments, the one or more endpoints may further comprise an electronic medical records server or third-party application server. The one or more instructions may further comprise instructions for analyzing the plurality of input data according to one or more scientific evaluation parameters to determine a measure of protocol compliance or deviation for the at least one user in the user population. Further still, the one or more instructions may comprise instructions for dynamically modifying or configuring the one or more computerized stimuli or interactions for a first user group in the two or more user groups according to the one or more scientific evaluation parameters.

Further aspects of the present disclosure provide for a computer-implemented system comprising at least one server comprising at least one processor, the at least one server implementing a plurality of functional modules configured to provide a plurality of scientific evaluation functions; an application server communicably engaged with the at least one server via a communications network, the application server hosting a software product configured to process a plurality of user inputs in response to one or more computerized stimuli or interactions to generate a targeted output for treatment, diagnosis or management of a medical or personal wellness condition; and a non-transitory computer readable storage medium operably engaged with the at least one processor and encoded with computer-executable instructions that, when executed by the at least one processor, perform a method for scientific evaluation of the software product, the method comprising establishing a communication interface and data transfer protocol between the application server and the at least one server, the data transfer protocol being configured to enable secure transmission of mobile endpoint data to the at least one server, wherein the mobile endpoint data comprises user-generated data from a user device executing an instance of the software product; configuring one or more scientific evaluation parameters for the software product comprising one or more usage or session parameters for one or more users of the software product, wherein the one or more users comprise a user population; providing one or more instance of the software product to the user device for the one or more users in the user population in accordance with the one or more scientific evaluation parameters; receiving mobile endpoint data and user-generated data for the one or more users in the user population; processing the mobile endpoint data and user-generated data according to an analytical framework to determine one or more user statistics and one or more stimulus-input patterns for the one or more users in the user population, the one or more user statistics and the one or more stimulus-input patterns comprising user outcome data; and analyzing the user outcome data for the user population according to at least one statistical framework to determine one or more scientific validation metrics for the targeted output of the software product.

In accordance with said aspects of the present disclosure, the method for scientific evaluation of the software product encoded on the non-transitory computer readable medium may further comprise monitoring user adherence (e.g. protocol compliance or deviation) to the one or more scientific evaluation parameters. The method may further comprise segmenting the user population into two or more user groups according to the one or more scientific evaluation parameters, wherein the one or more scientific evaluation parameters comprise a first set of parameters for a first user group and a second set of parameters for a second user group in the two or more user groups. Certain embodiments of the computer-implemented system of the present disclosure may further comprise at least one third-party application server being communicably engaged with the at least one server via a communications network, the at least one third-party application server being configured to execute at least one scientific evaluation function.

In accordance with certain aspects of the present disclosure, the method for scientific evaluation of the software product encoded in the non-transitory computer readable medium may further comprise modifying the one or more computerized stimuli or interactions or revoking access to the software product according to one or more scientific evaluation parameters. The method may further comprise providing one or more notifications to the user device according to the one or more scientific evaluation parameters, the one or more notifications comprising user instructions or user prompts for executing an instance of the software product. In accordance with certain embodiments, the one or more notifications are provided to the user device according to one or more user adherence rules.

Still further aspects of the present disclosure provide for a computer-implemented system comprising at least one server comprising at least one processor, the at least one server implementing a plurality of functional modules configured to provide a plurality of scientific evaluation functions; an application server communicably engaged with the at least one server via a communications network, the application server hosting a software product configured to process a plurality of user inputs in response to one or more computerized stimuli or interaction to generate a targeted output for treatment, diagnosis or management of a medical or personal wellness condition; and a non-transitory computer readable storage medium operably engaged with the at least one processor and encoded with computer-executable instructions that, when executed by the at least one processor, perform a method for scientific evaluation of the software product, the method comprising establishing a communication interface and data transfer protocol between the application server and the server, the data transfer protocol being configured to enable secure transmission of mobile endpoint data to the server, wherein the mobile endpoint data comprises user-generated data from a user device executing an instance of the software product; configuring one or more clinical evaluation parameters for the software product comprising one or more safety, efficacy or performance parameters for the software product; providing one or more instance of the software product to the one or more user devices at two or more time points; receiving the user-generated data and the mobile endpoint data from the one or more user devices; processing the user-generated data and the mobile endpoint data according to an analytical framework to determine one or more user statistics and one or more stimulus-input patterns for each user in the user population, the one or more user statistics and the one or more stimulus-input patterns comprising user outcome data; and analyzing the user outcome data according to at least one statistical framework to determine one or more safety, efficacy or performance metrics for the software product.

In accordance with said aspects of the present disclosure, the method for scientific evaluation of the software product encoded on the non-transitory computer readable medium may further comprise modifying or configuring the one or more computerized stimuli or interactions in response to the one or more safety, efficacy or performance metrics. The method may further comprise processing the user-generated data and the mobile endpoint data in response to modifying or configuring the one or more computerized stimuli or interactions, and analyzing the user outcome data according to the at least one statistical framework to determine a measure of change in the one or more safety, efficacy or performance metrics. The method may further comprise further modifying or configuring the one or more computerized stimuli or interactions in response to the measure of change in the one or more safety, efficacy or performance metrics.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be recognized by those skilled in the art that such equivalent structures do not depart from the spirit and scope of the invention.

BRIEF DESCRIPTION OF DRAWINGS

The above and other objects, features and advantages of the present disclosure will be more apparent from the following detailed description of, and in conjunction with, the accompanying drawings, which are briefly described below.

DETAILED DESCRIPTION

Figure 1:
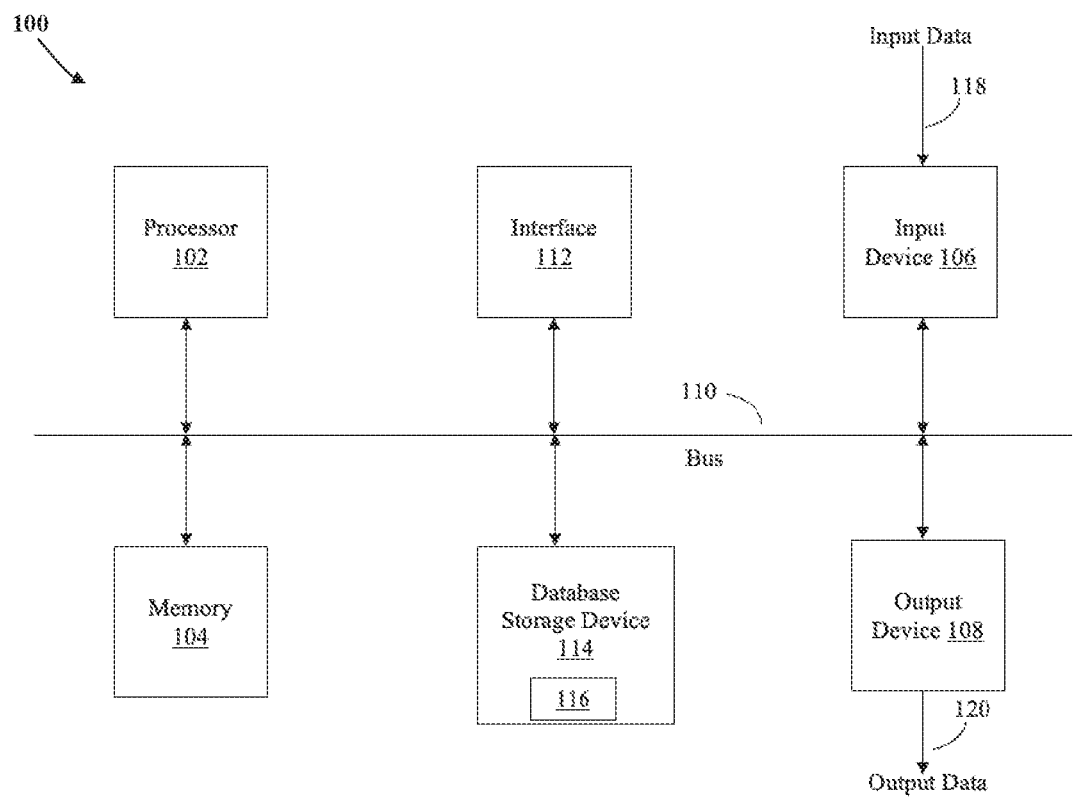
FIG. 1 is a functional block diagram of an exemplary computing system through which certain aspects of the present disclosure may be implemented.

Exemplary embodiments are described herein so as to provide a more detailed description of the invention. Variations of the various embodiments will be apparent to those of skill in the art. Therefore, before specific exemplary embodiments of the invention are described, it is to be understood that this invention is not limited to the exemplified embodiments described herein. It is also to be understood that the terminology used herein is for the purpose of describing certain specific embodiments and is not intended to limit the scope of the invention which is defined only by the appended claims.

Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology. Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

As used in certain examples herein, the term "healthcare provider" encompasses one or more of a physician (including a pediatrician and/or a behavioral specialist), a nurse, a physician's assistant, a psychologist, a psychiatrist, and the supporting clinical and administrative office staff of a healthcare or medical facility.

As used in certain examples herein, the term "user" encompasses one or more of an end user of a software program, product or platform and may further include: a patient being engaged with a software program, product or platform for a targeted medical or personal wellness purpose; a participant in a clinical trial, study or evaluation of a software program, product or platform; a user being engaged with a software program, product or platform for the purpose of evaluating or developing one or more technical, clinical, and/or functional aspects of a digital health intervention and/or a software as a medical device program, product or platform.

As used herein the terms "software program," "software product," and "software platform" may be used interchangeably and may be used to described one or more software program, product or platform, including any product(s), program(s) and/or platform(s) that incorporate any combination of hardware and software, being designed and/or utilized for any targeted medical or personal wellness purpose, including but not limited to the treatment, diagnosis, management, prevention, cure, or generation/provision of clinical/health/wellness insights or recommendations to one or more users for one or more medial, health or personal wellness purpose; including one or more digital health intervention (DHI) and/or software as a medical device (SaMD); and may further include software that is itself directly therapeutically active in treating and/or targeting one or more neurological circuits related to one or more neurological, psychological and/or somatic conditions, diseases, and/or disorders, rather than just being a component of overall treatment.

As used herein the term "digital health intervention (DHI)" may be used interchangeably with software as a medical device (SaMD) and encompasses any software program, product, or platform, including any software/hardware combination, being designed and/or utilized for any targeted medical or personal wellness purpose, including but not limited to the treatment, diagnosis, management, prevention, cure, or generation/provision of clinical/health/wellness insights or recommendations to one or more users for one or more medial, health or personal wellness purpose; including any software program, product, or platform, including any software/hardware combination, being designed and/or utilized to promote healthy behaviors, improve outcomes in people with long term conditions such as cardiovascular disease, diabetes and mental health conditions and provide remote access to effective treatments; for example, computerized cognitive behavioral therapy for mental health and somatic problems; and may further encompass one or more software program, product or platform, including any product(s), program(s) and/or platform(s) that incorporate any combination of hardware and software, that is/are directly therapeutically active in treating and/or targeting one or more neurological circuits related to one or more neurological, psychological and/or somatic conditions, diseases, and/or disorders, rather than just being a component of overall treatment.

As used herein the term "software as a medical device (SaMD)" may be used interchangeably with the term digital health intervention (DHI) and encompasses any software program, product, or platform, including any software/hardware combination, being designed and/or utilized for any targeted medical or personal wellness purpose, including but not limited to the treatment, diagnosis, management, prevention, cure, or generation/provision of clinical/health/wellness insights or recommendations to one or more users for one or more medial, health or personal wellness purpose; and may further encompass any software program, product, or platform, including any software/hardware combination, intended to be used for one or more medical purposes that perform these purposes without being part of a hardware medical device; and may further encompass one or more software program, product or platform, including any product(s), program(s) and/or platform(s) that incorporate any combination of hardware and software, that is/are directly therapeutically active in treating and/or targeting one or more neurological circuits related to one or more neurological, psychological and/or somatic conditions, diseases, and/or disorders, rather than just being a component of overall treatment.

As used in certain examples herein, the term "patient" encompasses a user being engaged with a software program, product or platform for a targeted medical or personal wellness purpose, indication, and/or intended use.

As used in certain examples herein, the term "stakeholder" encompasses a manufacturer of software program, product or platform; an administrative user of a software program, product or platform; and may further include one or more of a healthcare provider, researcher, investigator, reviewer, administrator, parent, custodian, guardian or other caregiver of a patient.

As used in certain examples herein, the terms "investigator," "administrator," or "researcher," encompass a user or stakeholder being engaged with a software program, product or platform for the purpose of evaluating or developing one or more technical, clinical, and/or functional aspects of the software program, product or platform; and may further include a user or stakeholder being engaged with a software program, product or platform for the purpose of conducting a scientific evaluation, such as a clinical trial.

As will be appreciated by one of skill in the art, embodiments of the present disclosure may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

All definitions, as defined and used herein, should be understood to control over dictionary definitions, definitions in documents incorporated by reference, and/or ordinary meanings of the defined terms. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

Following below are more detailed descriptions of various concepts related to, and embodiments of, inventive methods, devices and systems for collecting, processing and analyzing a plurality of endpoint data to assess one or more functional, scientific, and/or clinical aspects of a DHI/SaMD program, platform or product. Certain embodiments provide for a platform to analyze user-generated data from a DHI/SaMD program, platform or product to determine one or more safety, efficacy, performance, and/or patient outcome metrics associated with one or more program code output and/or functional aspects of the DHI/SaMD. Certain embodiments further provide for a platform to design and facilitate the administration of a research study, clinical evaluation, and/or clinical trial for a DHI/SaMD program, platform or product. Certain embodiments further provide for a platform to continuously monitor and analyze a plurality of endpoint data to verify and improve safety, efficacy, and/or performance of a DHI/SaMD.

Certain embodiments provide for a system for configuring and administering a clinical trial for a DHI/SaMD program, platform or product. Such embodiments may comprise system and methods for the secured collection and analysis of data, and the secured sharing of content between disparate systems and platforms for the purpose of configuring and administering the clinical trial. The content can be, but is not limited to, the collected data and/or the results of the data analysis.

Certain embodiments of the present disclosure can be coupled with one or more types of measurement components, for receiving and analyzing data collected from at least one measurement of the one or more measurement components. As non-limiting examples, the measurement component can be a physiological component.

Certain embodiments of the present disclosure can be coupled with one or more types of cognitive platforms, for analyzing data collected from user interaction with the cognitive platform. As non-limiting examples, the cognitive platform and/or platform product can be configured for cognitive monitoring, cognitive assessment, cognitive screening, and/or cognitive treatment, including for clinical purposes. The data from the cognitive platform can be used by the exemplary systems, methods, and apparatus disclosed herein as symptom measurement data.

Certain embodiments of the present disclosure can be implemented to facilitate testing, monitoring and/or improved treatment of a variety of different conditions, such as but not limited to neuropsychological conditions, including dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or executive function disorders, including attention deficit hyperactivity disorder (ADHD), sensory-processing disorder (SPD), mild cognitive impairment (MCI), Alzheimer's disease, multiple-sclerosis, schizophrenia, major depressive disorder (MOD), or anxiety.

In a non-limiting example, certain embodiments of the present disclosure can be configured to facilitate testing, monitoring and/or improved treatment of ADHD. Symptoms of ADHD include inattentiveness, impulsivity and hyperactivity. Both children and adults can have ADHD, however, the symptoms can be exhibited beginning in childhood. ADHD can be considered a chronic disease in certain aspects. Once diagnosed, it is typically treated with medications and managed through behavioral therapies.

In an example, certain embodiments of the present disclosure can be configured to collect and analyze content that assist with monitoring progress and/or modifying the individual's treatment plan. In another example, certain embodiments of the present disclosure can be configured to assist in improving the results of a treatment using visualizations.

In another example, certain embodiments of the present disclosure can be configured as an application ("App") for use by a user or stakeholder. The scientific evaluation platform in this example can be configured to provide secured, authenticated access for the collection of data. The clinical trials platform gives parent, custodian, guardian or other caregiver of the child the capability to control the level and type of access that another user can have to the platform, thereby facilitating the collection of data through a secured access (such as but not limited to a secured login).

In this non-limiting exemplary implementation, the scientific evaluation platform may be configured such that an individual (including a parent, custodian, or other caregiver of an individual) may download an aspect of it as an App and use the App to collect data about the individual (including the child) on a regular basis. The App provides reminders and encouragement to ensure consistent, long-term engagement by the individual (including a parent, custodian, or other caregiver of an individual). The App is configured to provide the primary user the capability to request behavior data from another designated user (such as but not limited to a teacher or other caregiver of the individual). The request may be sent through a secured invitation delivered via email or other means. As an example, when the other, secondary user receives the invitation, they access the secure link provided, provide the information requested to set up an account (such as but not limited to login credentials) to be accessed at intervals to enter data and other information in the measurement fields provided (such as but not limited to information on how the child is behaving in school or to quantify measures of the individual's symptoms).

In non-limiting examples of a scientific evaluation platform for use in ADHD, the type of behavior metrics that are quantified can be behavior metrics related frequency and quality of homework assignment completion, frequency and quality of performing chores, and the quality of getting along with the parents, custodians, guardians, or other individual acting on behalf of a child. The exemplary symptom metrics can be set using scores from other symptom trackers.

The scientific evaluation platform is configured to allow a primary user to work with a healthcare provider to determine the type of test, system, or device to be presented in the measurement fields of the clinical trials platform and quantified using the platform.

The exemplary scientific evaluation platform allows users (such as but not limited to parent, teacher, physicians, behavioral therapists, etc.), to provide quantifiable measures of a variety of symptoms, also captures data from actual treatments (such as but not limited to scores from a cognitive treatment and other treatment), analyzes the collected data, an generates an enhanced analysis report that presents the data and analysis results in a form of interpretable, meaningful metrics, which can be used to determine if treatment is progressing adequately or satisfactorily.

An enhanced analysis report can be used in consultation with a healthcare provider to evaluate the individual's response to the treatment, determine any modifications to be made to the treatment, the overall time period for implementation of the modifications to the treatment, etc., in order to derive a stable outcome or an improved outcome of the treatment for the individual. This can result in a better condition management (including disease management) outcome for the individual.

In any example herein, the scientific evaluation platform provides control settings such that the access level and permissions for a secondary user set by a primary user may be revoked or overruled. While the examples are described relative to behavior measures or symptom measures, other types of measures are also applicable to the scientific evaluation platform.

Turning now to the drawings, FIG. 1 depicts an exemplary computing system according to which certain illustrated embodiments of the present invention may be implemented. The processing system 100 generally comprises at least one processor 102, a memory 104, an input device 106 for receiving input data 118 and an output device 108 that produces output data 120 coupled together with at least one bus 110. In certain embodiments, input device 106 and output device 108 could be the same device. An interface 112 can also be provided for coupling the processing system 100 to one or more peripheral devices, for example interface 112 could be a PCI card or PC card. At least one database storage device 114 which houses at least one database 116 can also be provided. The memory 104 can be any form of memory device, for example, volatile or non-volatile memory, solid state storage devices, magnetic devices, etc. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1 may operate in a networked environment using logical connections to one or more remote computers. The remote computer may be a personal computer, a server, a router, a network PC, a peer device, or other common network node, and typically includes many or all of the elements described above. It is to be further appreciated that the logical connections depicted in FIG. 1 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which various embodiments of the invention may be implemented. FIG. 1 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system 100 of FIG. 1. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments of the present invention can be implemented with numerous other general-purpose or special-purpose computing devices, systems or configurations. Examples of well-known computing systems, environments, and configurations suitable for use in embodiment of the invention include, personal computers, handheld or laptop devices, personal digital assistants, multiprocessor systems, microprocessor-based systems, set top boxes, programmable consumer electronics, network, minicomputers, server computers, game server computers, web server computers, mainframe computers, and distributed computing environments that include any of the above systems or devices.

Various embodiments of the invention will be described herein in a general context of computer-executable instructions, such as program modules, being executed by a computer. Generally, program modules include routines, programs, objects, components, data structures, etc., that perform particular tasks or implement particular abstract data types. In certain embodiments, distributed computing environments where tasks are performed by remote processing devices that are linked through a communications network may also be employed. In distributed computing environments, program modules may be located in both local and remote computer storage media including memory storage devices.

With the general computing system environment 100 of FIG. 1 being shown and discussed above, the following description and remaining figures pertain to various exemplified embodiments of the present invention generally relating to methods for data analysis and scientific evaluation of program code outputs in software as a medical device products and digital interventions. In general, the methods described herein involve analyzing, for the at least one user in the user population, a stimulus-response pattern between the one or more computerized stimuli or interactions and the plurality of user-generated inputs at two or more time points to determine one or more performance metrics for the at least one user in the user population; analyzing the plurality of input data and the one or more performance metrics to determine one or more user outcome metrics for the at least one user in the user population; analyzing, according to a validation model, the one or more computerized stimuli or interactions and the one or more user outcome metrics to determine one or more efficacy metrics associated with the targeted medical output; and outputting the one or more user outcome metrics and the one or more efficacy metrics to one or more administrator devices.

Figure 2:
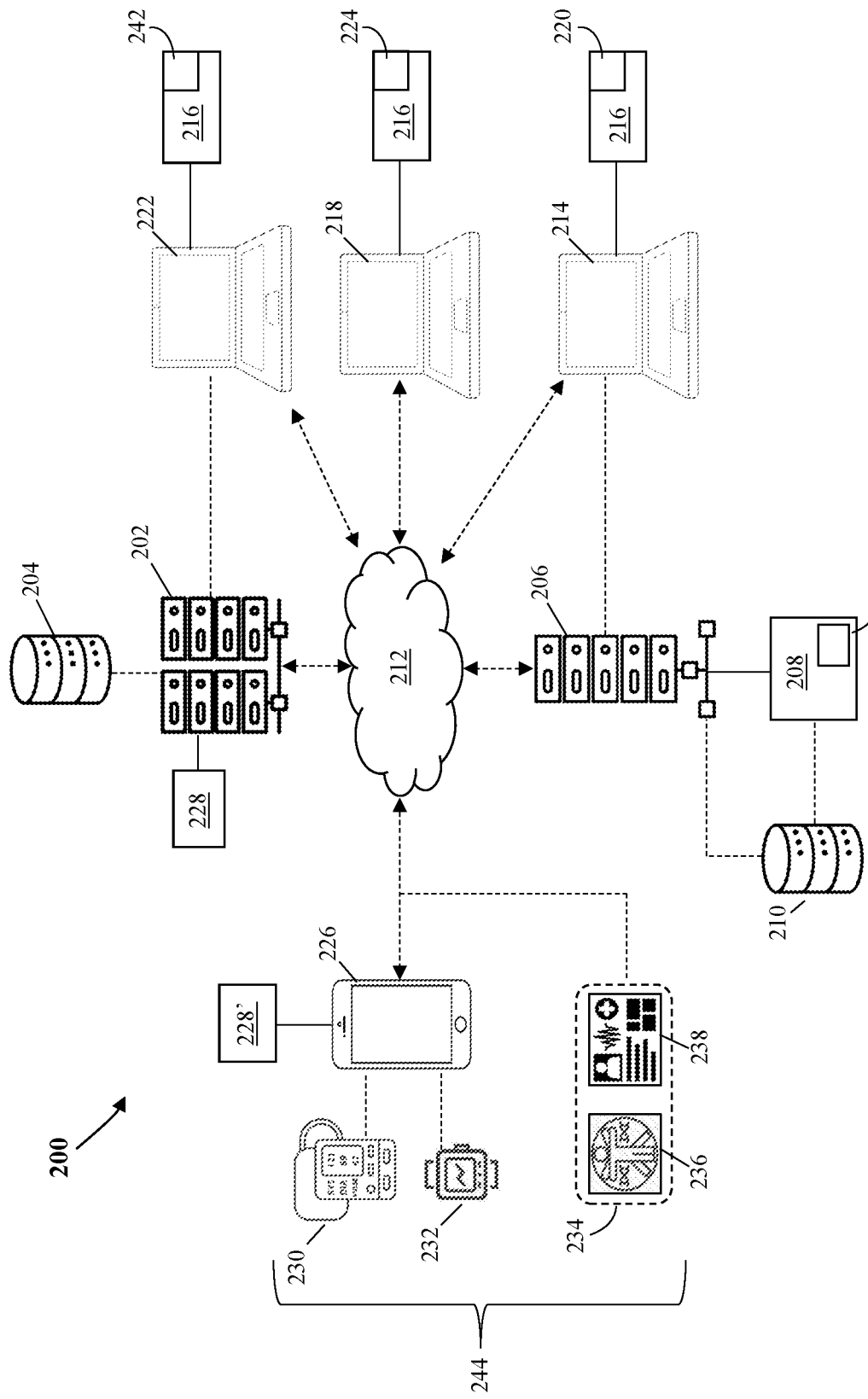
FIG. 2 is an architecture diagram of a system for scientific evaluation of a software product, in accordance with certain aspects of the present disclosure.

Referring now to FIG. 2, an architecture diagram of a system 200 for scientific evaluation of a software product is shown.

In accordance with certain aspects of the present disclosure, system 200 is generally comprised of a scientific evaluation platform server 206, a scientific evaluation engine 208, a platform database 210 and an administrator client 214. Scientific evaluation engine 208 may comprise a scientific evaluation platform product 240 configured to provide a scientific evaluation application 216 to one or more client devices across system 200. Administrator client 214 may be operably engaged with platform server 206 to execute an instance of scientific evaluation application 216, which may optionally comprise an administrator interface 220.

Platform server 206 may be communicably engaged with a manufacturer server 202, a plurality of endpoints 244, and one or more client devices 218 via communications network 212. Client device(s) 218 may be configured to execute an instance of scientific evaluation application 216, which may optionally be configured to render a researcher/investigator user interface 224.

In accordance with certain embodiments, manufacturer server 202 is operably engaged with a manufacturer database 204 to host and execute a server-side instance of a software product 228 comprising one or more digital health intervention (DHI) and/or software as a medical device (SaMD) product. Manufacturer server 202 may be operably engaged with manufacturer client 222 to control and/or configure one or more aspects of software product 228. Manufacturer client 222 may be communicably engaged with platform server 206 via communications network 212 to execute an instance of scientific evaluation application 216, which may optionally be configured to render a manufacturer user interface 242. In accordance with certain embodiments, a computing device 226 may be communicably engaged with manufacturer server 202 via communications network 212 to execute an instance 228' of software product 228. In some embodiments, computing device 226 may comprise a smartphone or tablet computer having one or more sensors and a touchscreen interface. Instance 228' may comprise a series of computerized stimuli or interactions (CSIs) comprising one or more user prompts being associated with a DHI/SaMD output. Software product 228 may be configured to receive and process/aggregate data from endpoints 244. Endpoints 244 may comprise one or more of biological/physiological measurement device 230 (e.g., an EEG machine, heartrate monitor, blood pressure cuff, continuous glucose monitoring (CGM) system, etc.), a mobile/wearable electronic device configured to measure one or more activity inputs and/or physiological measurements of a user (e.g., a smart watch or wearable activity monitor comprising one or more heart rate sensor, inertial or motion sensor, acoustic transducer, touch interface, and the like), and one or more external data sources 234 including, but not limited to, a laboratory information management system (LIMS) 236 and/or electronic medical record (EMR) system 238.

In accordance with certain aspects of the disclosure, system 200 is configured to enable scientific evaluation of software product 228. In certain embodiments, scientific evaluation engine 208 and scientific evaluation platform product 240 are operably configured with platform server 206 and platform database 210 to analyze one or more safety, efficacy, performance, and/or quality assurance aspects of the program code for software product 228. In further embodiments, scientific evaluation engine 208 and scientific evaluation platform product 240 are operably configured with platform server 206 and platform database 210 to enable configuration and administration of a distributed clinical trial for software product 228. In further embodiments, scientific evaluation engine 208 and scientific evaluation platform product 240 are operably configured with platform server 206 and platform database 210 to enable scientific evaluation of one or more outputs of software product 228 for one or more medical or clinical intended use.

In accordance with certain embodiments, scientific evaluation engine 208 is configured to process and analyze data from endpoints 244 according to one or more analytical frameworks. In certain embodiments, scientific evaluation engine 208 may process and analyze data from endpoints 244 according to one or more supervised or unsupervised, linear or non-linear, dimension reduction and/or data aggregation framework. Suitable dimension reduction and data aggregation frameworks include, without limitation: Principal Component Analysis (PCA), Multi-Dimension Scaling (MDS), Locally Linear Embedding (LLE), Independent Component Analysis, and Linear Discriminant Analysis. In certain embodiments, reducing dimensionality of input data comprises applying a PCA algorithm, resulting in output data that is orthogonal in the vector space.

In certain embodiments, reducing dimensionality of input data comprises applying a Manifold Learning method to identify one or more non-linear structure(s) in the data. Manifold Learning methods are particularly useful for identifying high dimensional structures of raw input data from the data itself, without use of predetermined classifications.

In further embodiments, MDS is employed for projecting high dimensionality data into a lower dimensional surface. In such embodiments, observations include a similarity distance delta for input into the algorithm. Outcomes are provided as vectors of coordinates for each data point in a x-dimensional with the objective being to find representatives of K for a given input data set. The representatives of K are called "cluster centers" or "centroids," and are selected so as to have a minimum distance from each data point to a centroid in the same.

In still further embodiments, a lower dimension projection of a selected data set is identified or located using LEE, which preserves distances (location) within local neighborhoods. Furthermore, dimensionality of labeled data can be achieved using supervised methods, such as Linear Discriminant Analysis and/or Neighborhood Component Analysis.

In accordance with certain embodiments, scientific evaluation engine 208 is further configured to clean some or all input data before processing the input data for analysis. Exemplary data cleaning techniques employed by scientific evaluation engine 208 may include, without limitation, imputation, capping, and flooring of the data. In accordance with certain embodiments, data cleaning by imputation may comprise the use of a decision tree. In one embodiment, one or more leaf node may comprise a class label with a majority of training examples reaching the leaf. In certain embodiments, each internal node represents a question on at least one feature of software product 228 that will be branching out according to each answer. Each answer generates a set of questions that aid to determine the data and decision-making based on it. The final result of decision tree indicates the possibility of all decision and outcome scenarios. In an alternative exemplary embodiment, K-nearest neighbor (KNN) may be employed for imputation of missing data. KNN defines a set of nearest neighbors of a sample and substitutes the missing data by calculating the average of non-missing values to its neighbors. Nearest neighbor is measured as the closest values based on the Euclidean distance.

In certain embodiments, a "Bayesian network" may be employed for data input in the compiling of a dataset. Specifically, compiling a dataset according to embodiments of the invention comprises employing one or more Bayesian network to apply additional independent constraints on variables so as to identify, in a concise manner, one or more probable relationship(s) between the variables. Using Bayesian networks for imputation offers several advantages, including the ability to handle missing data models encodes dependencies among all variables and the preservation of the joint probability distribution of the variables. A key element of the Bayesian approach is that missing data is incorporated as an added unknown quantity in estimating a posterior distribution, with the posterior distribution being defined as the total knowledge of integration between prior distribution and likelihood function to a parameter after its been observed. In certain embodiments, particularly in models sensitive to high data input values, data cleaning may comprise calculating the mean (variance) by a method of capping and flooring of the input dataset or observations at one or more specific percentiles (e.g., 1% or 99%).

Figure 3:
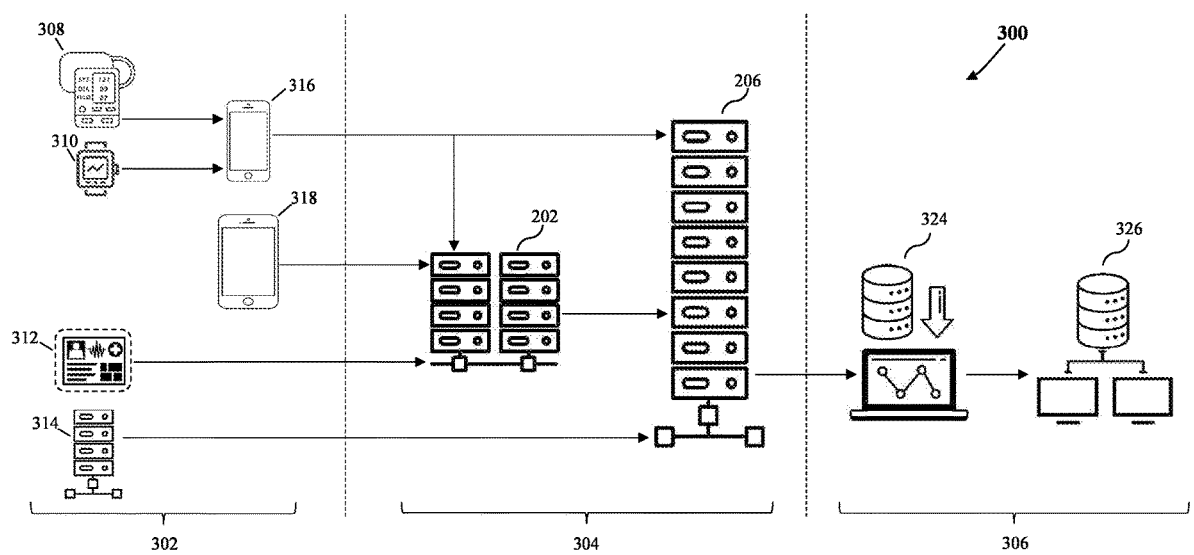
FIG. 3 is a data flow diagram of a system for scientific evaluation of a software product, in accordance with certain aspects of the present disclosure.

Referring now to FIG. 3, a data flow diagram of a system 300 for scientific evaluation of a software product is shown. In accordance with certain aspects of the present disclosure, system 300 is operably configured to collect data from a plurality of endpoints 302, receive and process data via one or more servers 304, and analyze and manage the data across one or more client devices 306. In accordance with certain embodiments, a software product is a DHI/SaMD being hosted on a manufacturer server 202 and being provided to at least one computing device 316,318. A platform server 206 is configured to host and execute a scientific evaluation application being configured to establish a data transfer interface and data transfer protocols between endpoints 302, manufacturer server 202, and platform server 206. Endpoints 302 may include at least one computing device 316,318 comprising a tablet computer, a mobile phone, a personal computer, and the like, executing an instance of the software product comprising DHI/SaMD. In certain embodiments, endpoints 302 may further include one or more connected devices 308,310 being operably configured with a computing device 316. For example, computing device 316 may be communicably engaged with a physiological or biological sensor device 308 (e.g., an EEG machine, heart-rate monitor, blood pressure cuff, continuous glucose monitoring (CGM) system, etc.) and/or a mobile/wearable electronic device 310 configured to measure one or more activity inputs and/or physiological measurements of a user (e.g., a smart watch or wearable activity monitor comprising one or more heart rate sensor, inertial or motion sensor, acoustic transducer, touch interface, and the like). Endpoints 302 may further include one or more patient data sources 312 including electronic medical record system(s) and laboratory information management system(s). Endpoints 302 may further include one or more third-party servers, such as an EMR server, LIMS server, and one or more third-party application servers. In some embodiments, endpoints 302 may be configured to have a direct data transfer interface with platform server 206. In some embodiments, endpoints 302 may be configured to have a direct data transfer interface with manufacturer server 202, wherein manufacturer server 202 may be configured to communicate endpoint data to platform server 206. In some embodiments, some endpoints 302 may be configured to transfer data directly to manufacturer server 202 and other endpoints 302 may be configured to transfer data directly to platform server 206.

Still referring to FIG. 3, in accordance with certain embodiments, endpoint data received by manufacturer server 202 is communicated to platform server 206 in accordance with one or more data transfer protocols between manufacturer server 202 and platform server 206. Platform server 206 processes the endpoint data and provides the endpoint data to platform engine 324 for analysis. In accordance with certain embodiments, platform engine 324 comprises a platform database operably engaged with platform server 206 and a platform application executing on platform server 206 being configured to process the endpoint data according to one or more scientific evaluation modules.

The output of platform engine 324 is provided to one or more client devices 326 executing a client-side instance of the platform application for scientific evaluation of the software product.

Figure 4:
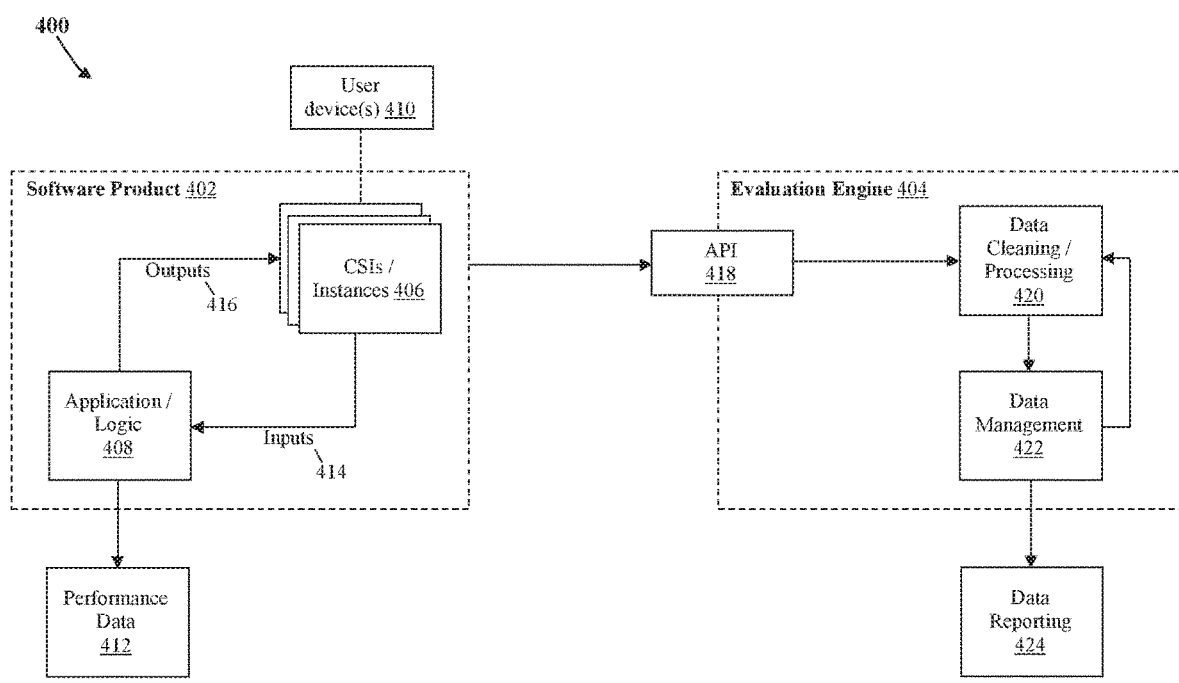
FIG. 4 is a functional block diagram of a system for scientific evaluation of a software product, in accordance with certain aspects of the present disclosure.

Referring now to FIG. 4, a functional block diagram of a system 400 for scientific evaluation of a software product 402 is shown. In accordance with certain aspects of the present disclosure, software product 402 is a DHI/SaMD product being operably configured for at least one intended medical or clinical use or purpose. Software product 402 is functionally configured to enable said at least one intended medical or clinical use or purpose via one or more application instances/CSIs 406 being provided to one or more user devices 410. Software product 402 comprises a series of processor-executable instructions comprising application/program logic 408 being stored and executed on a computing device (e.g. a smart phone or tablet computer) and/or being provided to the computing device by a remote server over a communications network. Application/program logic 408 is operably configured to render one or more application instances/CSIs 406 to user devices 410; receive one or more user-generated inputs 414 in response to the one or more application instances/CSIs 406; process the one or more user-generated inputs 414 according to application/program logic 408; and render one or more application outputs 416 to user devices 410 via the application instances/CSIs 406. Application/program logic 408 is operably configured to continuously process user inputs 414 and render/deliver one or more application outputs in accordance with the intended medical or clinical use or purpose for the user. Application/program logic 408 may be operably configured to provide one or more performance data outputs 412 corresponding to user inputs 414 in response to the one or more application instances/CSIs 406 for the purpose of assessing or measuring user performance/outcomes in association with the intended medical or clinical use or purpose of software product 402.

In accordance with certain embodiments and still in reference to FIG. 4, evaluation engine 404 is communicably engaged with software product 402 via application programming interface (API) 418 to receive program output data and user input data from software product 402. Evaluation engine 404 is configured to process, and optionally clean, the data received via API 418 via one or more computational/analytical frameworks. Certain data cleaning techniques suitable for use in various embodiments include, without limitation, imputation, capping, and flooring of the data. Data processing 420 may be dynamically configured according to one or more scientific evaluation parameters being configured to analyze one or more dependent variables associated with the intended medical or clinical use or purpose of software product 402. Evaluation engine 404 is further configured to execute one or more data management operations 422 configured to segment, classify, and/or analyze the data according to the scientific evaluation parameters. Evaluation engine 404 is configured to render and output the data for data reporting 424. Data reporting 424 may enable structured and dynamic reporting of the data to one or more client devices for the purpose of evaluating the data according to the one or more scientific evaluation parameters. Evaluation engine 404 and data reporting 424 are operably configured to provide a quantitative and qualitative analysis of the data for the purpose of assessing the validity and integrity of one or more associations between the intended medical, clinical and/or personal wellness use or purpose of software product 402 and user performance data and/or user outcome data generated via user interaction with software product 402.

Figure 5:
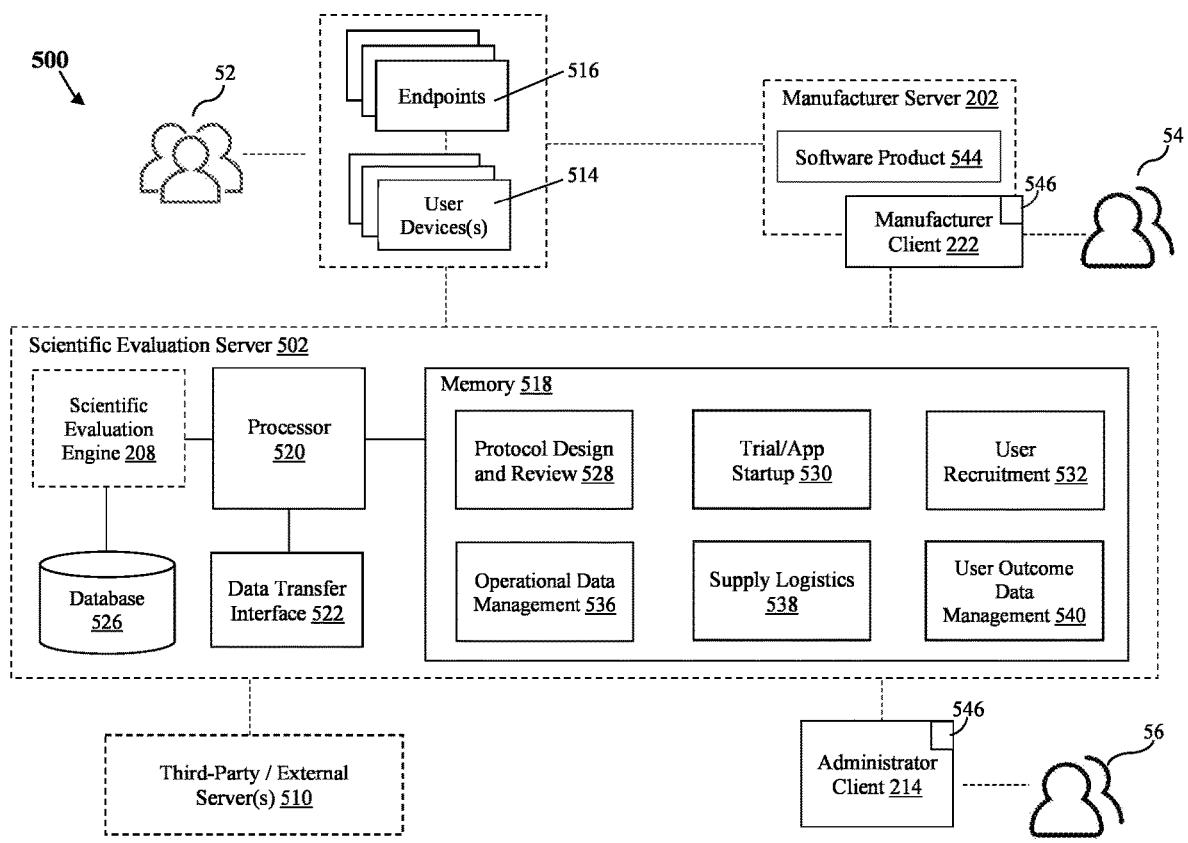
FIG. 5 is a functional block diagram of a system for scientific evaluation of a software product, in accordance with certain aspects of the present disclosure.

Referring now to FIG. 5, a functional block diagram of a system 500 for scientific evaluation of a software product 544 is shown. In accordance with certain aspects of the present disclosure, a scientific evaluation server 502 is communicably engaged with a manufacturer client 202, an administrator client 214, one or more user devices 514 executing an instance of software product 514, one or more mobile or server-based endpoints 516, and one or more third party and/or external servers 510. Scientific evaluation server 502 may be comprised of a processor 520, a data transfer interface 522, a scientific evaluation engine 208, a database 526, and a non-transitory memory device 518 having stored thereon instructions comprising one or more functional modules being operably configured to cause processor 520 to execute one or more scientific evaluation functions. In certain embodiments, the one or more functional modules are operably configured to enable setup and administration of a distributed clinical trial for software product 544. The one or more functional modules may comprise a protocol design and review module 528, a trial/application startup module 530, a user recruitment module 532, an operational data management module 536, a supply logistics module 538, and a user outcome data management module 540.

In accordance with certain embodiments, protocol design and review module 528 may comprise operations for configuring and executing one or more protocol design and review functions, including one or more functions for: trial/evaluation design; trial/evaluation methodology; selection and/or training of data model(s); user permissions and access/usage parameters; data segmentation and assessment of functional areas (e.g. safety, efficacy, performance, etc.); protocols for adverse event handling; quality control and assurance parameters; and data management and reporting parameters. Trial/application startup module 530 may comprise one or more operations for configuring and executing one or more trial/application startup functions, including one or more functions for: user onboarding (e.g. secure account creation, first time user experience, user instructions and messaging, and user consent(s)) and user demographic/information prompts; user reimbursement setup, including electronic linking of user bank account (for trials or evaluations in which a user is reimbursed for time and/or expenses); user authentication parameters and protocols; and data transfer interface and protocols, including endpoint selection and interface. User recruitment module 532 may comprise one or more operations for configuring and executing user recruitment functions, including one or more functions for: study support and study selection parameters; study signup workflow and parameters; study-specific consent terms and requirements. Operational data management module 536 may comprise operations for configuring and executing one or more operational data management functions, including one or more functions for: user assignment and segmentation; user notifications and communications; operational data processing and reporting; data security protocols and parameters; user activity and software usage parameters and notifications; administrative controls and access rights, including parameters for lack of use, revoking access, or removal/bricking of software or specific features; adverse event tracking and handling; and data transfer interface with third-party systems. Supply logistics module 538 may comprise one or more operations for configuring and executing one or more supply logistics functions, including one or more functions for: software product acquisition; parallel authentication/login framework; and additional application acquisition. User outcome data management module 540 may comprise one or more operations for configuring and executing user recruitment functions, including one or more functions for: data rendering and reporting; data collection parameters and data transfer protocols; selection and/or training of data model(s); data segmentation and cleaning; and data access and data query parameters.

In accordance with certain aspects of the present disclosure and still in reference to FIG. 5, system 500 is operably configured to enable scientific evaluation and/or clinical trial(s) of software product 544 across a plurality of client devices being communicably engaged with scientific evaluation server 502. In accordance with certain embodiments, software product 544 comprises a DHI/SaMD product being operably configured for at least one intended medical, clinical and/or personal wellness use or purpose. System 500 enables one or more administrator/evaluator user(s) 56 and/or one or more manufacturer user(s) 54 to configure and administer protocols for scientific evaluation, research study and/or clinical trial(s) of software product 544. In accordance with an embodiment, an administrator user 56 executes an instance of a scientific evaluation application 546 to configure and administer a scientific evaluation and/or a clinical trial for software product 544. Administrator user 56 establishes a data transfer interface and data transfer protocol between manufacturer server 202 and scientific evaluation server 502; and, optionally establishes a data transfer interface and data transfer protocol between one or more third-party/external server(s) 510 and scientific evaluation server 502. Additionally, administrator user 56 and/or manufacturer user 54 may establish a data transfer interface and data transfer protocol between user devices 514, endpoints 516 and scientific evaluation server 502. Administrator user 56 may configure and execute one or more scientific evaluation or clinical trial functions provided by scientific evaluation application 546 in accordance with the one or more functional modules.

In accordance with certain aspects of the present disclosure and still in reference to FIG. 5, system 500 is operably configured to administer a scientific evaluation, research study and/or clinical trial of software product 544. In accordance with certain embodiments, one or more users 52 may access an instance of software product 544 via user device(s) 514 according to one or more evaluation or trial parameters/protocols. In some embodiments, users 52 may be segmented and/or classified into one or more user groups defining a user population. Scientific evaluation server 502 receives user device data and endpoint data according to data transfer protocols configured within scientific evaluation application 546. Scientific evaluation server 502 may also receive one or more data inputs from the one or more third-party/external server(s) 510. Scientific evaluation engine 208 may be operably engaged with processor 520 to process the data inputs in accordance with the one or more functional modules. Scientific evaluation engine 208 may be further operably engaged with processor 520 to analyze the data inputs in accordance with the one or more functional modules. Scientific evaluation engine 208 may be further operably engaged with processor 520 to manage the data inputs and outcome data in accordance with the one or more functional modules. In accordance with certain embodiments, administrator client 214 and/or manufacturer client 222 may query and analyze the data inputs and outcome data via an instance of scientific evaluation application 546. Scientific evaluation application 546 may be configured to render and output one or more data visualizations and/or reports configured to enable administrator user(s) 56 and/or manufacturer user(s) 54 to evaluate one or more aspects of software product 544 according to the scientific evaluation and/or clinical trial parameters.

Figure 6:
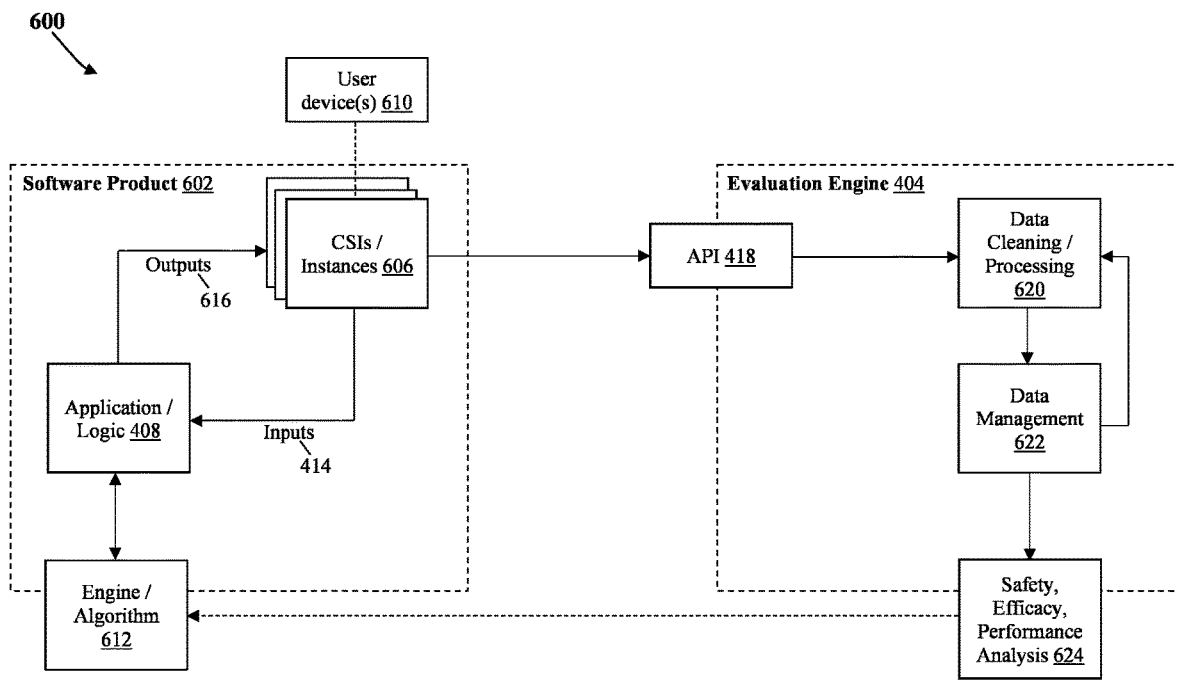
FIG. 6 is a functional block diagram of a system for scientific evaluation of a software product, in accordance with certain aspects of the present disclosure.

Referring now to FIG. 6, a functional block diagram of a system 600 for scientific evaluation of a software product 602 is shown. In accordance with certain aspects of the present disclosure, software product 602 is a DHI/SaMD product being operably configured for at least one intended medical, clinical and/or personal wellness use or purpose. Software product 602 is functionally configured to enable the at least one intended medical or clinical use or purpose via one or more application instances/CSIs 606 being provided to one or more user devices 610. Software product 602 comprises a series of processor-executable instructions comprising application/program logic 408 being stored and executed on a computing device (e.g. a smart phone or tablet computer) and/or being provided to the computing device by a remote server over a communications network. Application/program logic 408 is operably configured to render one or more application instances/CSIs 606 to user devices 610; receive one or more user-generated inputs 414 in response to the one or more application instances/CSIs 606; process the one or more user-generated inputs 414 according to application/program logic 408; and render one or more application outputs 616 to user devices 610 via the application instances/CSIs 606. Application/program logic 408 is operably configured to continuously process user inputs 414 and render/deliver one or more application outputs in accordance with the intended medical or clinical use or purpose for the user. Application engine/algorithm 612 may be operable to dynamically configure application/program logic 408 in response to inputs 414 in order to enable the at least one intended medical or clinical use or purpose of software product 602.

In accordance with certain embodiments and still in reference to FIG. 6, evaluation engine 404 is operable to analyze one or more safety, efficacy, and/or performance aspects of software product 602. Evaluation engine 404 may be communicably engaged with software product 602 via application programing interface (API) 418 to receive program output data and user input data from software product 602. Evaluation engine 404 is configured to process, and optionally clean, the data received via API 418 via one or more computational/analytical frameworks. Certain data cleaning techniques suitable for use in various embodiments include, without limitation, imputation, capping, and flooring of the data. Data processing/cleaning operations 620 may be dynamically configured according to one or more scientific evaluation parameters being configured to analyze one or more dependent variables associated with the intended medical, clinical and/or personal wellness use or purpose of software product 602. Evaluation engine 404 may be further configured to execute one or more data management operations 622 configured to segment, classify, and/or analyze the data according to the scientific evaluation parameters. In accordance with certain embodiments, the one or more scientific evaluation parameters comprise one or more safety, efficacy, or performance parameters. Evaluation engine 404 may analyze the data according to the one or more safety, efficacy, and/or performance parameters to render and output a safety, efficacy, and/or performance analysis 624. Safety, efficacy, and/or performance analysis 624 may be configured to analyze and validate one or more aspects of engine/algorithm 612. In accordance with certain embodiments, safety, efficacy, and/or performance analysis 624 is configured to provide quantitative and qualitative measure(s) of the degree to which engine/algorithm 612 enables the at least one intended medical, clinical and/or personal wellness use or purpose. In certain embodiment, safety, efficacy, and/or performance analysis 624 may be configured to provide a feedback loop to inform, reinforce, modify, and/or configure one or more aspects of the program code for engine/algorithm 612.

Figure 7:
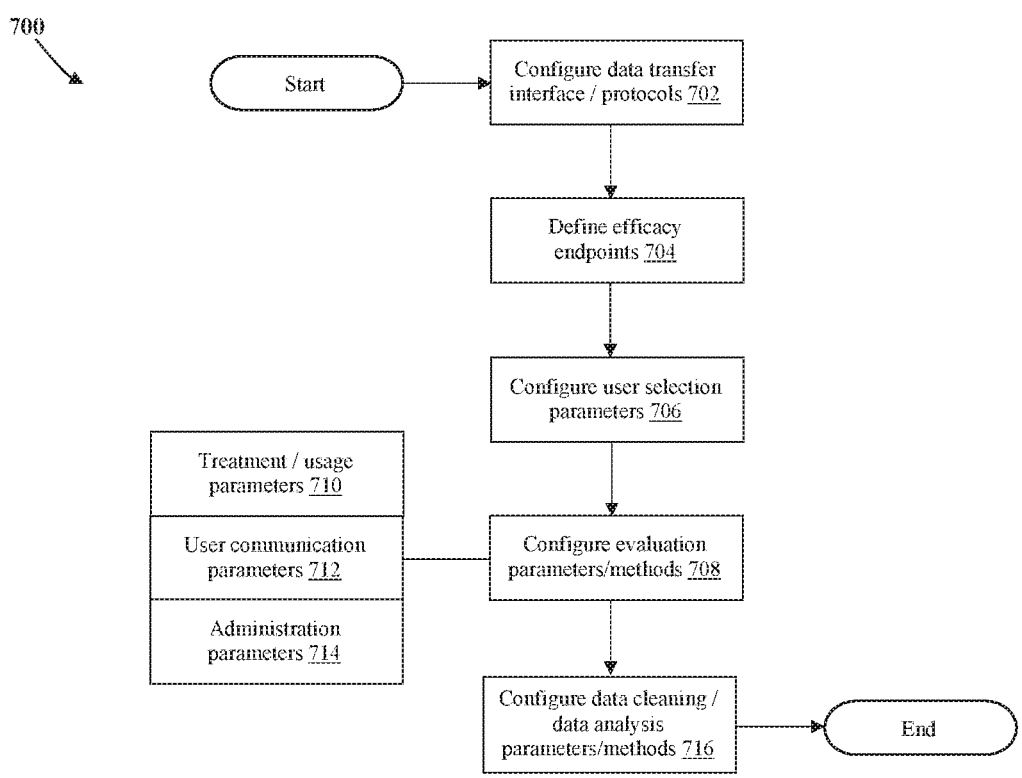
FIG. 7 is a functional block diagram of a routine for protocol design within a system for scientific evaluation of a software product, in accordance with certain aspects of the present disclosure.

Referring now to FIG. 7, a functional block diagram of a routine 700 for protocol design within a system for scientific evaluation of a software product is shown. In accordance with certain embodiments, the software product is a DHI/SaMD product. In accordance with certain embodiments, routine 700 is embodied in one or more functional modules being stored on at least one non-transitory computer readable medium being executed by at least one processor within the system for scientific evaluation of the software product. In accordance with certain aspects of the present disclosure, routine 700 comprises one or more operations for configuring a scientific evaluation protocol, research study protocol, and/or clinical trial protocol within a scientific evaluation platform and/or application, which may comprise one or more of steps 702-716. In certain specific embodiments, routine 700 comprises configuring one or more data transfer protocols and data transfer interface (Step 702) between a scientific evaluation server and one or more user devices executing an instance of the software product to be evaluated and/or a manufacturer server of the software product. Routine 700 may further configure data transfer protocols and data transfer interface for one or more mobile/wearable devices, third-party servers and/or applications, and biological/physiological sensor devices. Data transfer protocols may be configured to communicate user-generated data, device data, and/or sensor data between the user devices, manufacturer server, and associated data sources to the scientific evaluation server. Routine 700 may continue by defining one or more efficacy endpoints of the software product to be evaluated by the scientific evaluation server (Step 704). In accordance with certain embodiments, the one or more efficacy endpoints are configured to validate or verify an association between one or more program code outputs of the software product and at least one intended medical, clinical and/or personal wellness use or purpose. Routine 700 may further comprise one or more safety and performance endpoints. Routine 700 may continue by configuring user selection parameters (Step 706) for a scientific evaluation, research study, and/or a clinical trial of the software product. Routine 700 may continue by configuring evaluation parameters/methods (Step 708) for the scientific evaluation, research study, and/or clinical trial of the software product. Evaluation parameters/methods may comprise treatment/usage parameters for the software product (Step 710); user communication parameters (Step 712) comprising system-generated communications/notifications and user/stakeholder communications during the scientific evaluation or clinical trial of the software product; and administration parameters (Step 714) for administration and management of the scientific evaluation or clinical trial of the software product. Routine 700 may continue by configuring one or more data cleaning, processing and analysis parameters and methods (Step 716).

Figure 8:
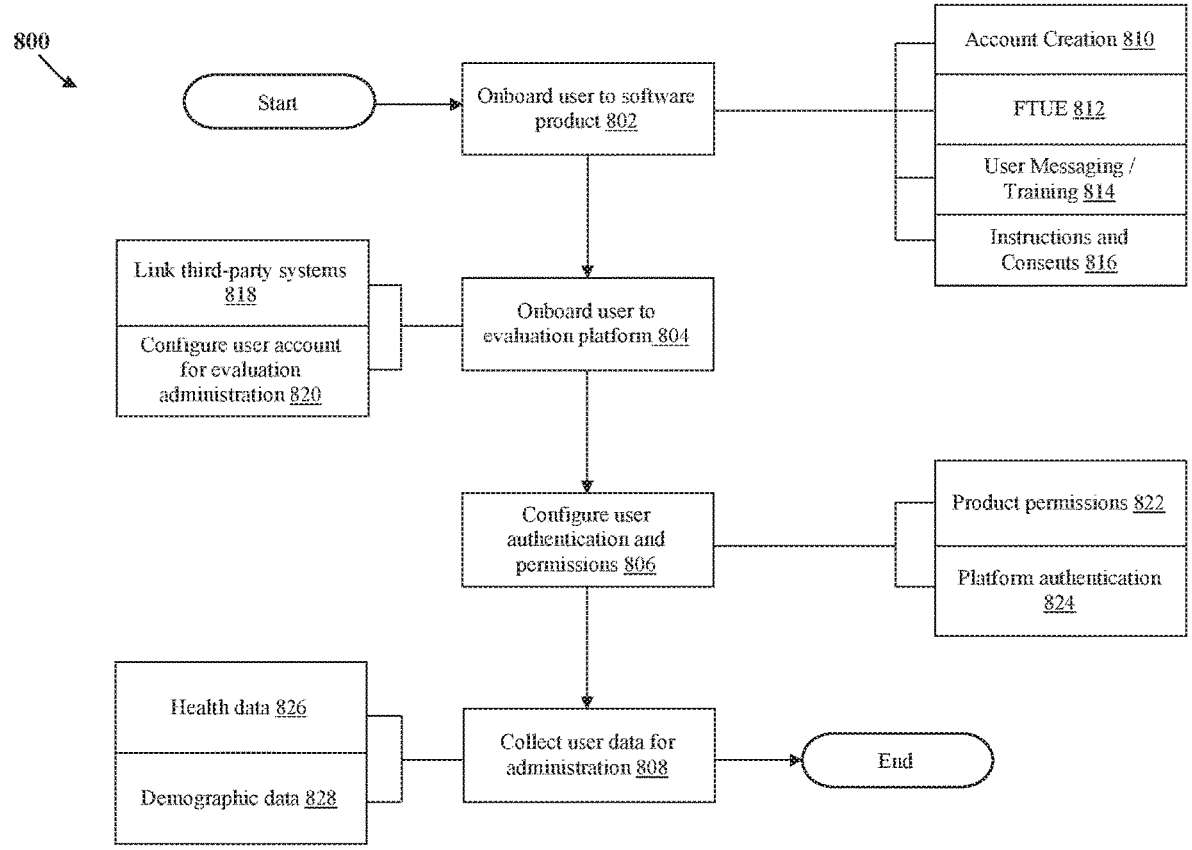
FIG. 8 is a functional block diagram of a routine for trial selection and startup within a system for scientific evaluation of a software product, in accordance with certain aspects of the present disclosure.

Referring now to FIG. 8, a functional block diagram of a routine 800 for scientific evaluation selection and startup within a system for scientific evaluation of a software product is shown. In accordance with certain embodiments, the software product is a DHI/SaMD product. In accordance with certain embodiments, routine 800 is embodied in one or more functional modules being stored on at least one non-transitory computer readable medium being executed by at least one processor within the system for scientific evaluation of the software product. In accordance with certain aspects of the present disclosure, routine 800 comprises one or more operations for configuring scientific evaluation selection and startup protocols and parameters within a scientific evaluation platform and/or application, which may comprise one or more of steps 802-828. In certain specific embodiments, routine 800 is initiated by executing a user onboarding workflow to onboard a user to the software product to be evaluated (Step 802). User onboarding may include one or more onboarding steps, including: account creation (Step 810); first time user experience instance (Step 812); presentation of one or more user messaging or user training (Step 814); and presentation of instructions related to scientific evaluation or clinical trial parameters and user consents (Step 816). Routine 800 may continue by executing the user onboarding workflow to onboard the user to a scientific evaluation platform (Step 804). The user onboarding workflow may further comprise one or more operations for linking third-party or external systems to the scientific evaluation server (Step 818); and configuring the user's account for administration of the scientific evaluation protocols, research study, or clinical trial (Step 820). Routine 800 may continue by configuring user authentication and permissions (Step 806), including configuring one or more product permissions (Step 822) and one or more platform authentication parameters (Step 824). Routine 800 may continue by executing one or more workflows to receive and process user data to be used in administration of the scientific evaluation or clinical trial (Step 808). In accordance with certain embodiments, user data may comprise user historical health data (Step 826) (e.g., electronic medical record data and/or laboratory information management system data) and user demographic data (Step 828).

Figure 9:
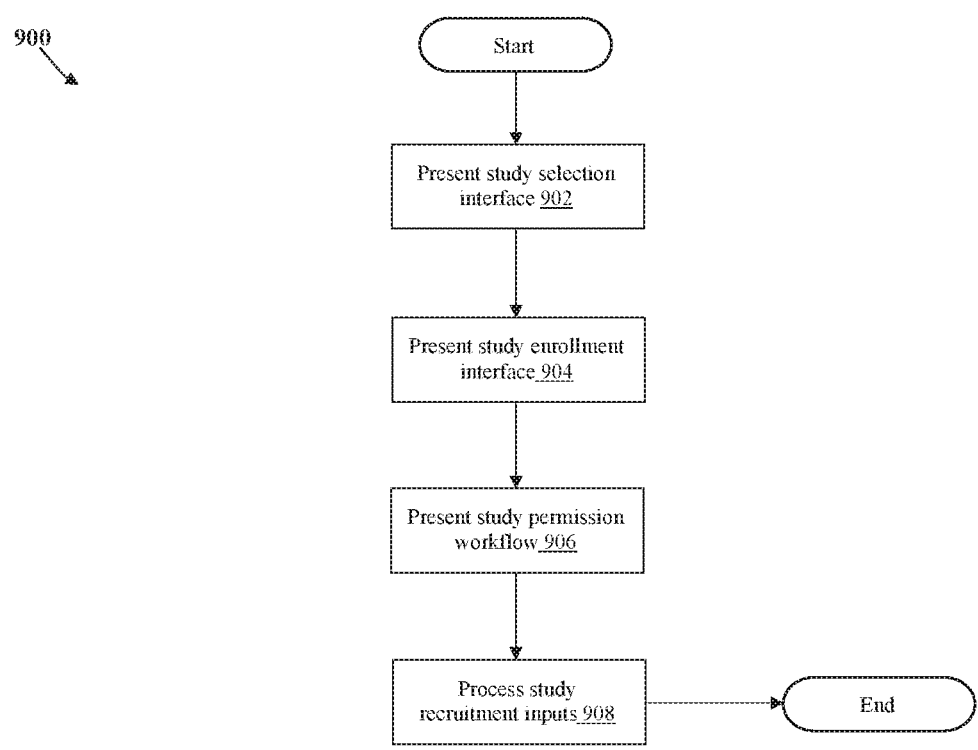
FIG. 9 is a functional block diagram of a routine for patient recruitment within a system for scientific evaluation of a software product, in accordance with certain aspects of the present disclosure.

Referring now to FIG. 9, a functional block diagram of a routine 900 for user recruitment within a system for scientific evaluation of a software product is shown. In accordance with certain embodiments, the software product is a DHI/SaMD product. In accordance with certain embodiments, routine 900 is embodied in one or more functional modules being stored on at least one non-transitory computer readable medium being executed by at least one processor within the system for scientific evaluation of the software product. In accordance with certain aspects of the present disclosure, routine 900 comprises one or more operations for user recruitment protocols and parameters within a scientific evaluation platform and/or application, which may comprise one or more of steps 902-908. In certain specific embodiments, routine 900 is initiated by presenting a study selection interface (Step 902) to a user of a scientific evaluation platform via at least one user device. In certain embodiments, the study selection interface may be configured to display one or more studies available for participation via the scientific evaluation platform. Routine 900 may continue by presenting a study enrollment interface (Step 904) to the user of the scientific evaluation platform via the at least one user device. In certain embodiments, the study enrollment interface may be configured to provide a study enrollment workflow configured to enable the user of the scientific evaluation platform to enroll in one or more studies via the scientific evaluation platform. Routine 900 may continue by presenting a study permission workflow (Step 906) to the user of the scientific evaluation platform via the at least one user device. In certain embodiments, the study permission workflow may comprise one or more steps to obtain study-specific consent from the user for user participation in the scientific evaluation, research study and/or clinical trial. Routine 900 may continue by processing the study recruitment inputs (Step 908) and either enrolling the user in the scientific evaluation, research study and/or clinical trial or excluding the user from the scientific evaluation, research study and/or clinical trial.

Figure 10:
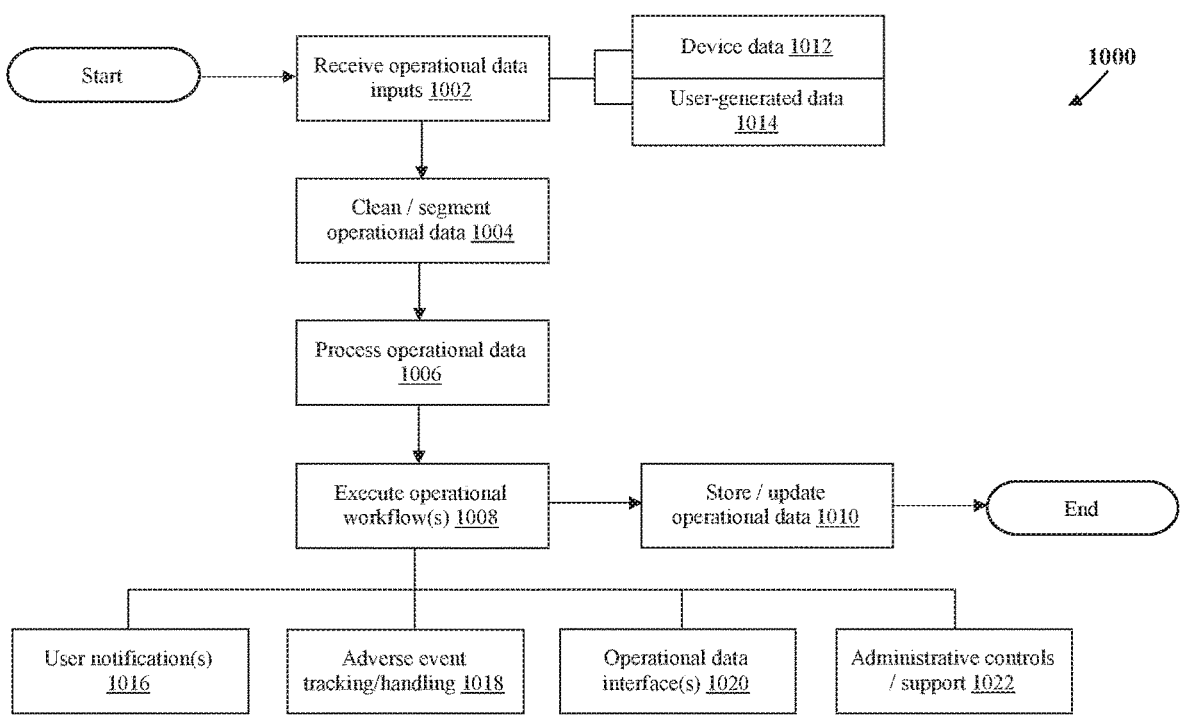
FIG. 10 is a functional block diagram of a routine for operational data management within a system for scientific evaluation of a software product, in accordance with certain aspects of the present disclosure.

Referring now to FIG. 10, a functional block diagram of a routine 1000 for operational data management within a system for scientific evaluation of a software product is shown. In accordance with certain embodiments, the software product is a DHI/SaMD product. In accordance with certain embodiments, routine 1000 is embodied in one or more functional modules being stored on at least one non-transitory computer readable medium being executed by at least one processor within the system for scientific evaluation of the software product. In accordance with certain aspects of the present disclosure, routine 1000 comprises one or more operations for operational data management protocols and parameters within a scientific evaluation platform and/or application, which may comprise one or more of steps 1002-1022. In certain specific embodiments, routine 1000 is initiated by receiving, with the scientific evaluation server in response to one or more instances and/or CSIs of the software product, one or more operational data inputs (Step 1002). The one or more operational data inputs may comprise device data (Step 1012) and/or user-generated data (Step 1014). Routine 1000 may proceed by cleaning and/or segmenting the operational data (Step 1004) according to one or more operational data management protocols. Routine 1000 may proceed by processing the operational data (Step 1006) according to one or more data processing models, framework, and/or rules engine. Routine 1000 may proceed by executing one or more operational workflows (Step 1008) in response to processing the operational data. In accordance with certain embodiments, the one or more operational workflows may comprise one or more user notification(s) (Step 1016); adverse event tracking/handling (Step 1018); operational data interface(s) (Step 1020); and administrative controls and support (Step 1022). Upon execution of one or more operational workflows in accordance to the data processing output, routine 1000 may continue by updating and storing the operational data in the platform database.

Figure 11:
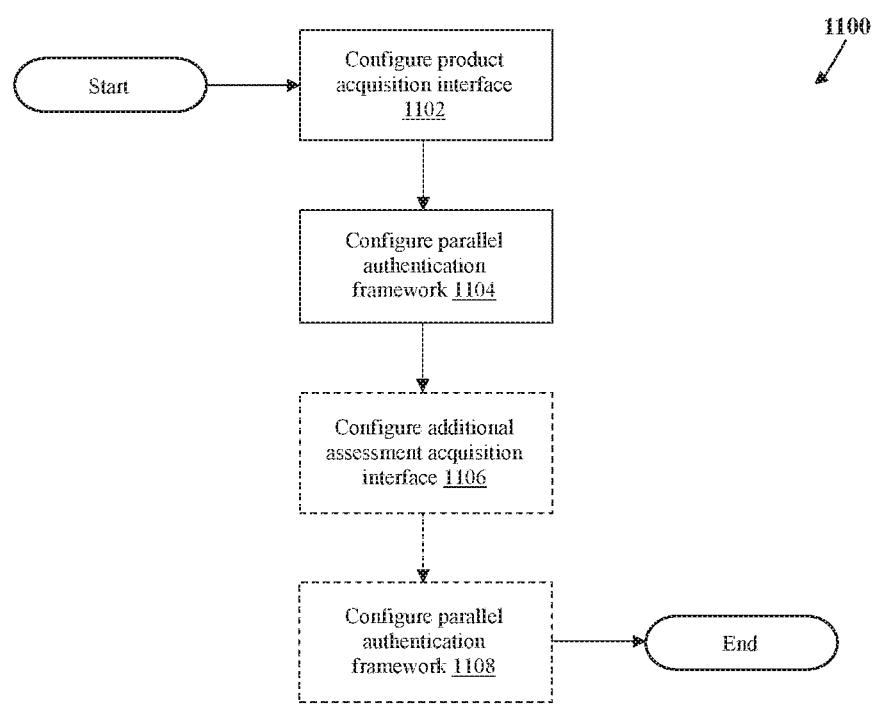
FIG. 11 is a functional block diagram of a routine for software delivery logistics within a system for scientific evaluation of a software product, in accordance with certain aspects of the present disclosure.

Referring now to FIG. 11, a functional block diagram of a routine 1100 for software delivery logistics within a system for scientific evaluation of a software product is shown. In accordance with certain embodiments, the software product is a DHI/SaMD product. In accordance with certain embodiments, routine 1100 is embodied in one or more functional modules being stored on at least one non-transitory computer readable medium and executed by least one processor within the system for scientific evaluation of the software product. In accordance with certain aspects of the present disclosure, routine 1100 comprises one or more operations for software delivery logistic protocols and parameters within a scientific evaluation platform and/or application, which may comprise one or more of steps 1102-1108. In certain specific embodiments, routine 1100 is initiated by configuring a product acquisition interface (Step 1102) for acquisition (e.g., download) by the user device of the software product that is the subject of the study or clinical trial. Routine 1100 continues by configuring a parallel authentication framework (Step 1104) for the software product. The parallel authentication framework may be configured to enable parallel authentication of the user across the manufacturer server and the scientific evaluation server. In certain embodiments in which one or more additional assessment and/or applications are to be assessed in conjunction with or as part of the study or clinical trial for the software product, routine 1100 continues by configuring an additional assessment acquisition interface (Step 1106) for the one or more additional assessments and/or applications. In such embodiments, routine 1100 may continue by configuring a parallel authentication framework (Step 1108) for the one or more additional assessments and/or applications.

Figure 12:
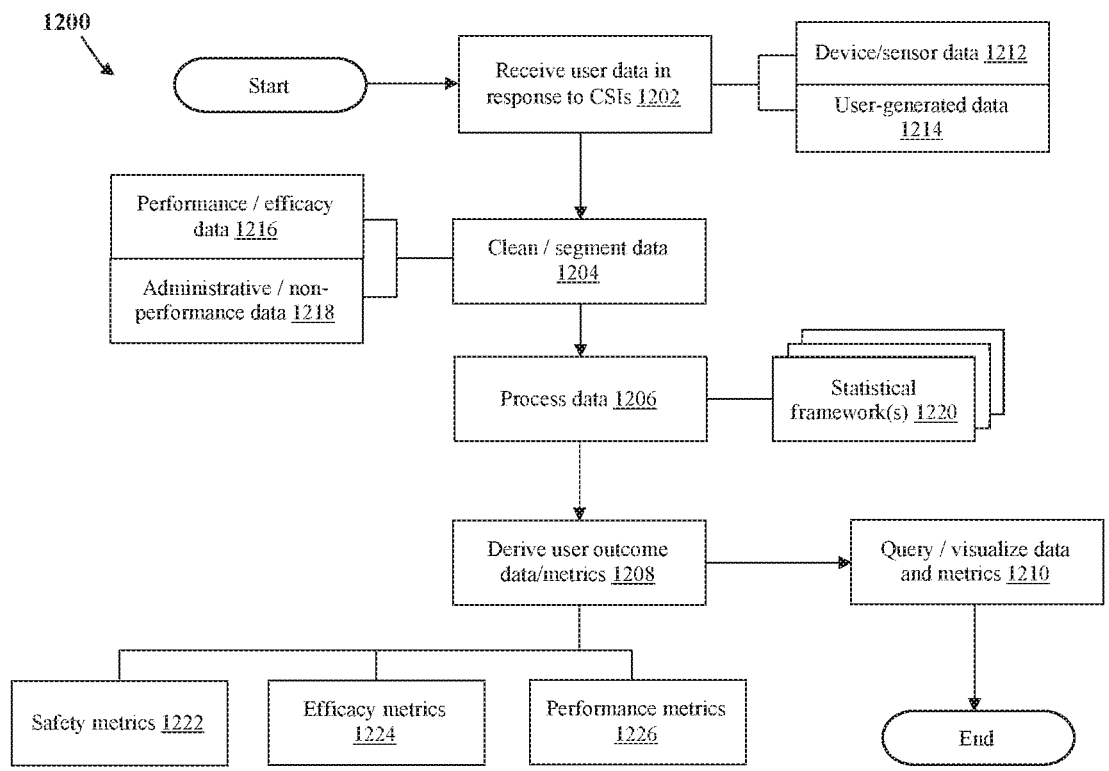
FIG. 12 is a functional block diagram of a routine for patient outcome data management within a system for scientific evaluation of a software product, in accordance with certain aspects of the present disclosure.

Referring now to FIG. 12, a functional block diagram of a routine 1200 for patient outcome data management within a system for scientific evaluation of a software product is shown. In accordance with certain embodiments, the software product is a DHI/SaMD product. In accordance with certain embodiments, routine 1200 is embodied in one or more functional modules being stored on at least one non-transitory computer readable medium and executed by at least one processor within the system for scientific evaluation of the software product. In accordance with certain aspects of the present disclosure, routine 1200 comprises one or more operations for patient outcome data management protocols and parameters within a scientific evaluation platform and/or application, which may comprise one or more of steps 1202-1226. In certain specific embodiments, routine 1200 is initiated by receiving, with the scientific evaluation server, user data in response to one or more CSIs being presented via the software product (Step 1202). The user data may comprise device/sensor data (Step 1212) and/or user-generated data (e.g., user inputs) (Step 1214). Routine 1200 may continue by cleaning and/or segmenting the user data in accordance with one or more data parameters and/or data processing protocols (Step 1204). In certain embodiments, the one or more data parameters and/or data processing protocols may comprise cleaning and segmenting the user data to differentiate between performance and efficacy data (Step 1216) and administrative or non-performance data (Step 1218). Routine 1200 may continue by processing the data (Step 1206) according to one or more statistical and/or analytical frameworks (Step 1220). The one or more statistical and/or analytical frameworks (Step 1220) may be configured according to the scientific evaluation or clinical trial parameters and may be configured to analyze one or more dependent variables associated with one or more safety, efficacy, and/or performance endpoints for the software product. In response to processing the data (Step 1206) according to the one or more statistical and/or analytical frameworks (Step 1220), routine 1200 may proceed by further processing the data to derive user outcome data and/or one or more user outcome metrics (Step 1208) based on the user data. In accordance with certain embodiments, the one or more user outcome metrics (Step 1208) may comprise one or more safety metrics (Step 1222), efficacy metrics (Step 1224), and/or performance metrics (Step 1226). Routine 1200 may proceed by querying the user outcome data in response to a request by an administrator user and rendering/presenting one or more data visualization and outcome metrics to the administrator user via a graphical user interface (Step 1210). In accordance with certain embodiment, step (Step 1210) is further configured to render and output one or more datasets according to one or more scientific evaluation, research study and/or clinical trial protocols.

Figure 13:
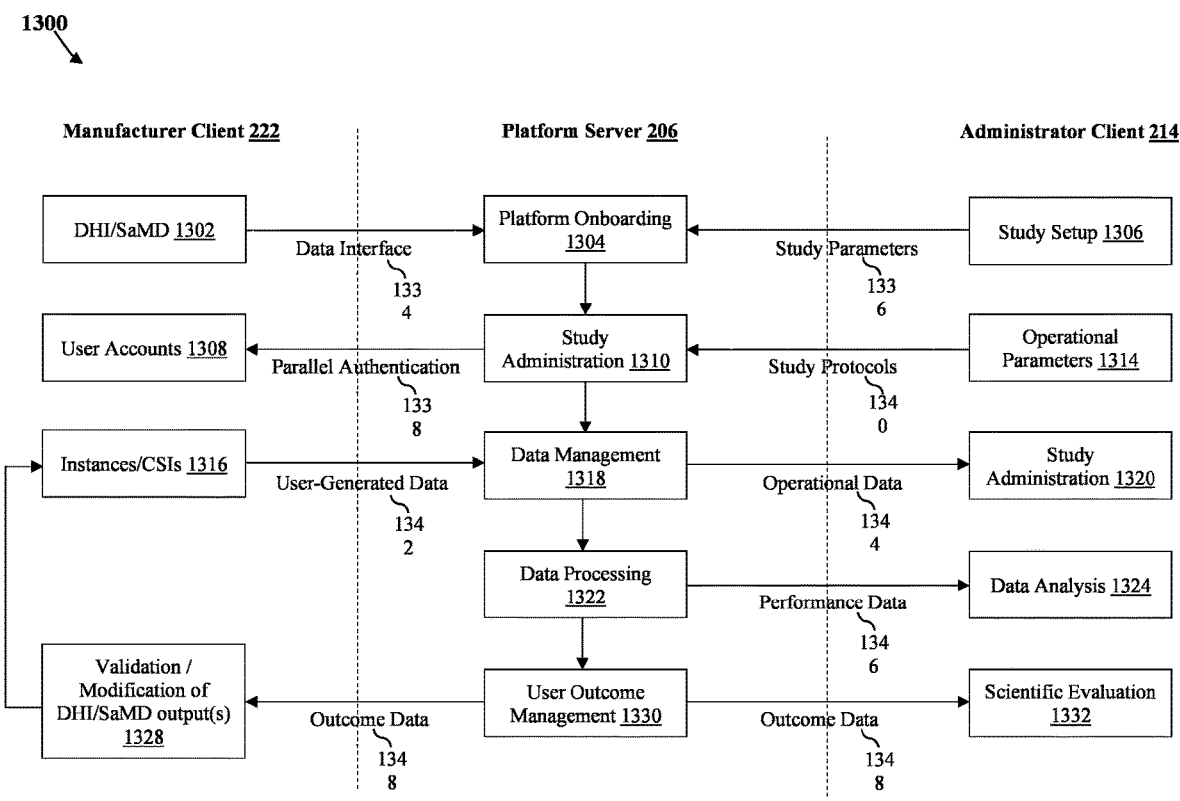
FIG. 13 is a functional block diagram of a routine for performance data analysis within a system for scientific evaluation of a software product, in accordance with certain aspects of the present disclosure.

Referring now to FIG. 13, a functional block diagram of a system 1300 for scientific evaluation (e.g., a study or clinical trial) of a DHI/SaMD 1302 is shown. In accordance with an embodiment, platform server 206 comprises a scientific evaluation platform and application for scientific evaluation of DHI/SaMD 1302. Manufacturer client 222 may be configured to host DHI/SaMD 1302 and provide DHI/SaMD 1302 to a plurality of user devices. Administrator client 214 may be communicably engaged with platform server 206 to selectively configure one or more protocols and parameters for administration of a scientific evaluation, research study and/or clinical trial related to DHI/SaMD 1302. In accordance with certain embodiments, system 1300 is operably configured to commence a scientific evaluation, research study and/or clinical trial of DHI/SaMD 1302 by executing a study setup workflow 1306 within a scientific evaluation application executing on administrator client 214. Study setup workflow 1306 is operably configured to receive and configure one or more study parameters 1336 within the scientific evaluation platform. Upon receiving the study parameters 1336, platform server 206 is operably configured to execute a platform onboarding workflow 1304. Platform onboarding workflow 1304 may comprise establishing a data transfer interface 1334 and one or more data transfer protocols between manufacturer client 222 and platform server 206. Data transfer interface 1334 may be operably configured to transfer data from DHI/SaMD 1302 to platform server 206 for processing and analysis. Upon completing the platform onboarding workflow 1304, platform server 206 may be operably configured to execute one or more study administration workflow(s) 1310. Administrator client 214 may configure one or more operational parameters 1314 via the scientific evaluation application executing on administrator client 214 and communicate one or more study protocols 1340 to platform server 206. Platform server 206 may configure one or more platform logic/operations according to study protocols 1340 and may configure a parallel authentication 1338 across manufacturer client and platform server for user accounts 1308. Upon completing the study administration workflow(s) 1310, platform server 206 may be operably configured to execute one or more data management operations 1318. Platform server 206 may be configured to receive user-generated data 1342 from manufacturer client 222 in response to one or more instances/CSIs 1316 associated with DHI/SaMD 1302. Platform server 206 may be configured to clean/segment user-generated data 1342 according to one or more data management parameters and render operational data 1344 to administrator client 214 via the scientific evaluation application. An administrative user may query operational data 1344 and view one or more data visualizations for operational data 1344 via the scientific evaluation application; and may execute one or more study administration workflows 1320 via the scientific evaluation application. Platform server 206 may be further configured to execute one or more data processing operations 1322 according to one or more data processing framework and render performance data 1346 to administrator client 214 via the scientific evaluation application. An administrative user may execute one or more data analysis operations 1324 in accordance with one or more scientific evaluation, research study and/or clinical trial protocols. Platform server 206 may be further configured to execute one or more user outcome management operations 1330 according to one or more user outcome management parameters. User outcome management operations 1330 may comprise providing outcome data 1348 to manufacturer client 1301. Manufacturer client 222 may be operably configured to execute operations for validation and/or modification of one or more program code outputs 1328 for DHI/SaMD. User outcome management operations 1330 may further comprise providing outcome data 1348 to administrator client 214 via the scientific evaluation application. In accordance with certain embodiments, the scientific evaluation application is operably configured to execute one or more scientific evaluation operations 1332 comprising one or more statistical analysis of one or more program code outputs 1328 for DHI/SaMD 1302. In accordance with certain embodiments, scientific evaluation operations 1332 may comprise evaluation of one or more safety, efficacy, performance, and/or quality assurance aspects for one or more program code outputs of DHI/SaMD 1302. In accordance with further embodiments, scientific evaluation operations 1332 may comprise rendering one or more study or clinical trial data outputs. In accordance with further embodiments, scientific evaluation operations 1332 may comprise analysis of one or more efficacy endpoints for DHI/SaMD 1302 according to the one or more medical or clinical intended use.

Figure 14:
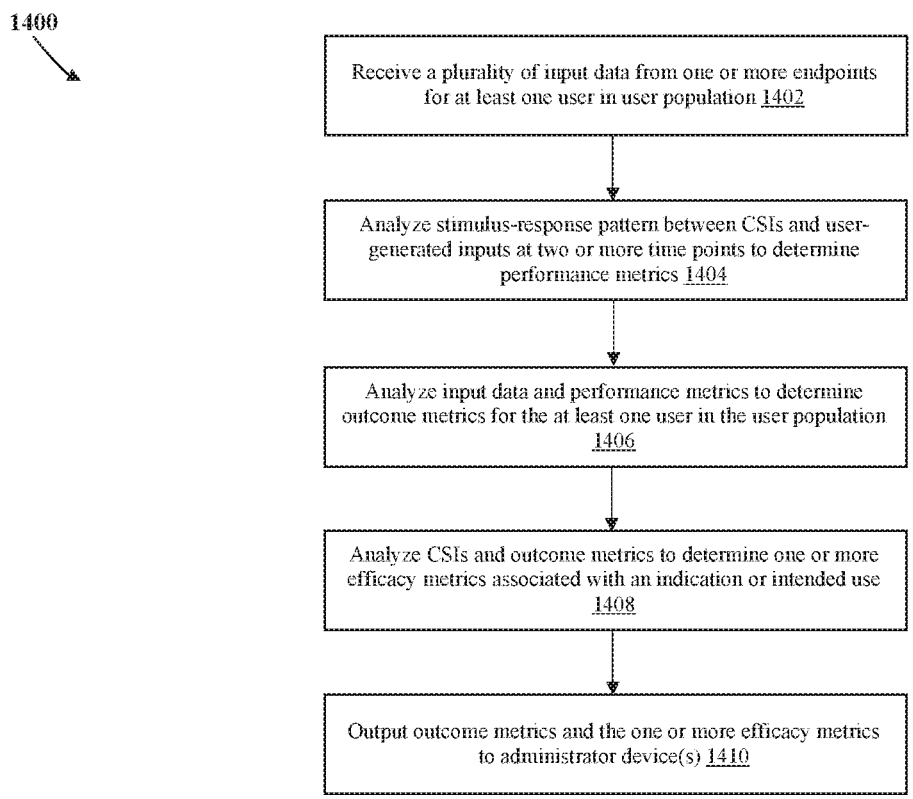
FIG. 14 is a process flow diagram of a method for scientific evaluation of a software product, in accordance with certain aspects of the present disclosure.

Referring now to FIG. 14, a process flow diagram of a method 1400 for scientific evaluation of a software product is shown. In accordance with certain embodiments, the software product is a DHI/SaMD product. In accordance with certain embodiments, method 1400 is embodied in one or more functional modules being stored on at least one non-transitory computer readable medium being executed by at least one processor within the system for scientific evaluation, research study and/or clinical trial for the software product. In accordance with certain aspects of the present disclosure, method 1400 comprises receiving, with a processor being operably engaged with a scientific evaluation server, a plurality of input data from one or more endpoints for at least one user in user population (Step 1402) in response to one or more user prompts or CSIs provided by the software product. In accordance with certain embodiments, the one or more endpoints comprise one or more user computing devices executing an instance of the software product. Method 1400 may continue by analyzing, with the processor according to a statistical framework, the processor and the statistical framework comprising a scientific evaluation engine, at least one stimulus-response pattern between the CSIs and the user-generated inputs at two or more time points to determine one or more performance metrics (Step 1404) for the software product. Method 1400 may continue by analyzing, with the scientific evaluation engine, the input data and performance metrics to determine one or more user outcome metrics for the at least one user in the user population (Step 1406). Method 1400 may continue further by analyzing, with the scientific evaluation engine, the CSIs and outcome metrics to determine one or more safety, efficacy and/or performance metrics associated with a primary indication or intended use for the software product (Step 1408). Method 1400 may continue further by rendering and outputting the outcome metrics and the one or more safety, efficacy and/or performance metrics to one or more administrator device(s) (Step 1410) for scientific evaluation and/or analytical validation of one or more program code outputs for the software product.

Figure 15:
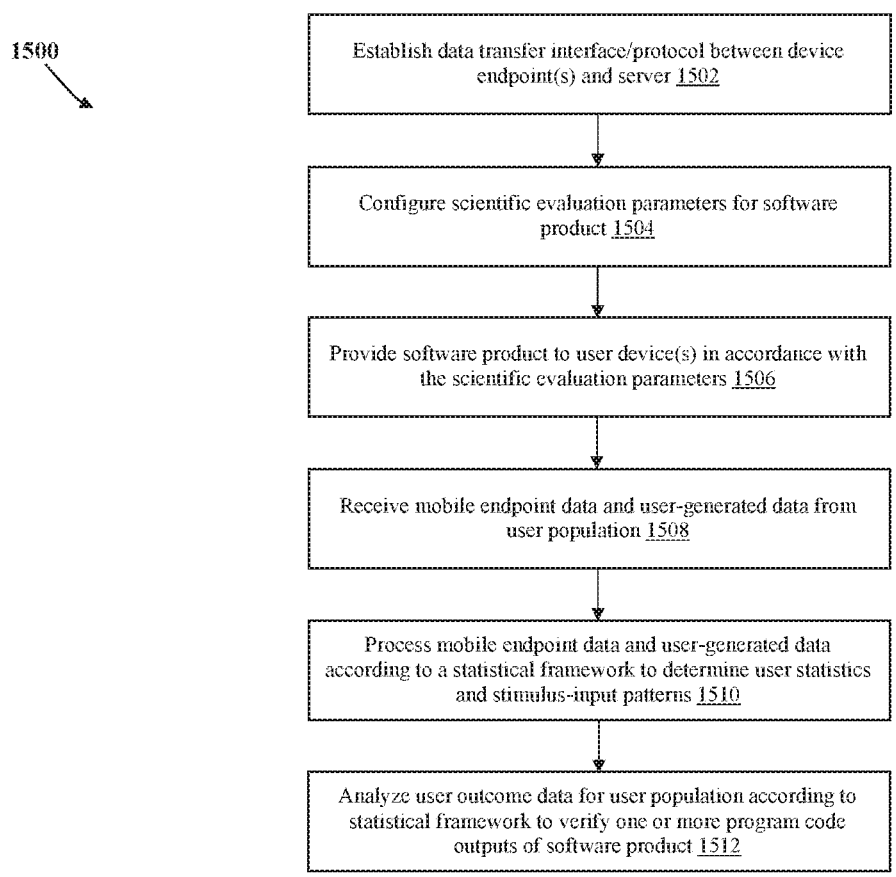
FIG. 15 is a process flow diagram of a method for scientific evaluation of a software product, in accordance with certain aspects of the present disclosure.

Referring now to FIG. 15, a process flow diagram of a method 1500 for scientific evaluation of a software product is shown. In accordance with certain embodiments, the software product is a DHI/SaMD product. In accordance with certain embodiments, method 1500 is embodied in one or more functional modules being stored on at least one non-transitory computer readable medium being executed by at least one processor within the system for scientific evaluation of the software product. In accordance with certain embodiments, method 1500 may be a continuation of method 1400. In accordance with certain aspects of the present disclosure, method 1500 comprises establishing data transfer interface/protocol between device endpoint(s) and a scientific evaluation server (Step 1502). Method 1500 may continue by configuring, with the scientific evaluation server, one or more scientific evaluation parameters for software product (Step 1504). Method 1500 may continue further by providing the software product to one or more user device(s) in accordance with the scientific evaluation parameters (Step 1506). In accordance with an embodiment, the one or more user devices comprise a user population. Method 1500 may continue further by receiving, with a processor being operably engaged with a scientific evaluation server, endpoint data and user-generated data from the one or more user device(s) in the user population (Step 1508). Method 1500 may continue further by processing, with the processor, the mobile endpoint data and user-generated data according to a statistical framework to determine user statistics and stimulus-input patterns (Step 1510), the processor and the statistical framework comprising a scientific evaluation engine. Method 1500 may continue further by analyzing, with the scientific evaluation engine, outcome data for the user population to determine/verify a valid association between one or more program code outputs for the software product (Step 1512) and the intended use/benefit of the software product.

Figure 16:
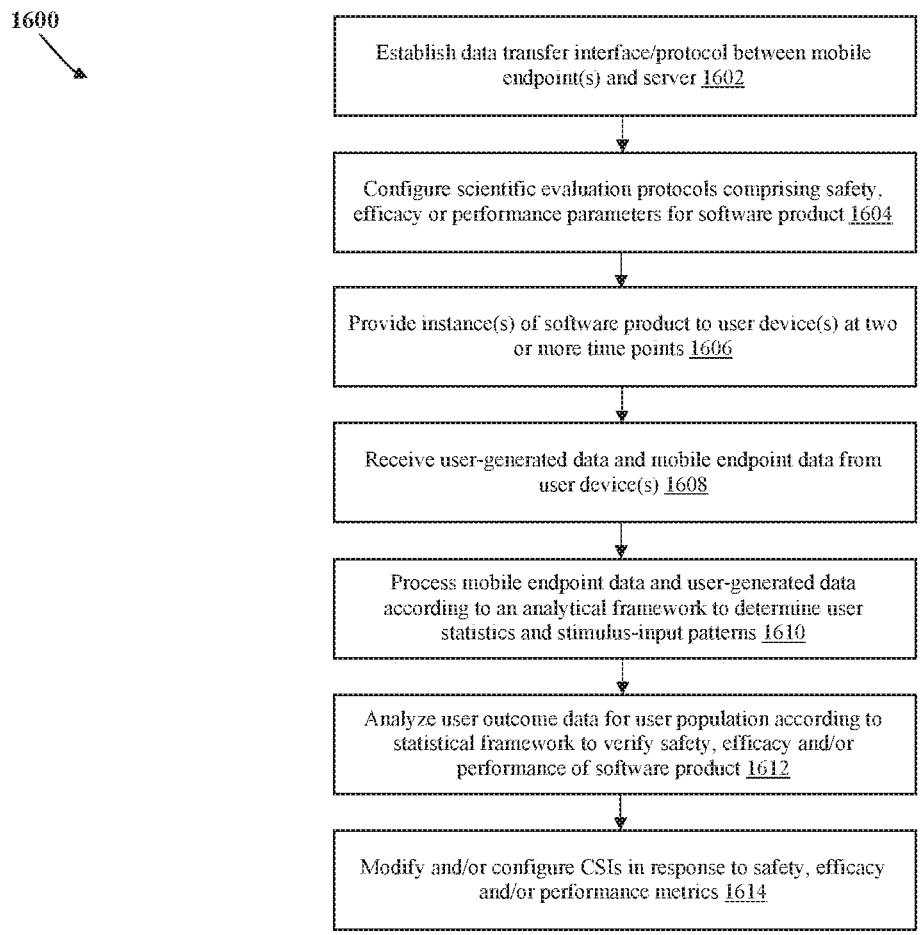
FIG. 16 is a process flow diagram of a method for scientific evaluation of a software product, in accordance with certain aspects of the present disclosure.

Referring now to FIG. 16, a process flow diagram of a method 1600 for scientific evaluation of a software product is shown. In accordance with certain embodiments, the software product is a DHI/SaMD product. In accordance with certain embodiments, method 1600 is embodied in one or more functional modules being stored on at least one non-transitory computer readable medium being executed by at least one processor within the system for scientific evaluation of the software product. In accordance with certain embodiments, method 1500 may be a continuation of method 1400 and/or 1500. In accordance with certain aspects of the present disclosure, method 1600 comprises establishing a data transfer interface and one or more data transfer protocols between a scientific evaluation server and one or more endpoints comprising at least one computing device executing an instance of the software product (Step 1602). Method 1600 may continue by configuring, with the scientific evaluation server, one or more scientific evaluation protocols comprising safety, efficacy and/or performance endpoints for software product (Step 1604). Method 1600 may continue further by providing, with a manufacturer server communicably engaged with the scientific evaluation server, one or more CSIs or instances of the software product to one or more user devices at two or more time points (Step 1606). In accordance with certain embodiments, the one or more user devices comprise a user population. Method 1600 may continue further by receiving, with a processor operably engaged with the scientific evaluation server, the user-generated data and device data from user devices (Step 1608). Method 1600 may continue further by processing, with the processor, the device data and user-generated data according to at least one statistical framework to determine one or more user statistics and stimulus-input patterns (Step 1610), the processor and the at least one statistical framework comprising a scientific evaluation engine. Method 1600 may continue further by analyzing, with the scientific evaluation engine, user outcome data for the user population to determine/verify one or more safety, efficacy and/or performance metrics for the software product (Step 1612). Method 1600 may continue further by modifying and/or configuring, with the manufacturer server being communicably engaged with the scientific evaluation server, the one or more CSIs for the software product according to the safety, efficacy and/or performance metrics (Step 1614).

It will be evident to persons skilled in the art that the above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

Additionally, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

Although embodiments of the invention have been described with a certain degree of particularity, it is understood that the present disclosure is provided by way of example and that various changes to details of construction or arrangement of parts and even steps may be made without departing from the spirit or scope of the invention. The terms and expressions used herein have been employed as terms of description rather than terms of limitation, and their use is not intended as excluding equivalents of the features or steps described thereby.

What is claimed is:

1. A computer-implemented method comprising:
providing, with an administrator client device, an instance of a scientific evaluation application to an administrative user, wherein the instance of the scientific evaluation application comprises a graphical user interface comprising one or more interface elements configured to selectively configure one or more protocols and parameters for scientific evaluation of a software product;
establishing, via the administrator client device, a real-time communication interface and data transfer protocol between an application server and at least one server, wherein the real-time communication interface and data transfer protocol comprises an application programming interface, wherein the data transfer protocol is configured to enable secure transmission of mobile endpoint data to the at least one server in real-time, wherein the mobile endpoint data comprises user-generated data from one or more user devices comprising a mobile electronic device executing an instance of the software product and a physiological sensor device configured to collect one or more physiological measurements of a user;
configuring, with the at least one server, a parallel authentication framework between the application server and the at least one server, wherein the parallel authentication framework is configured to authenticate, in parallel, one or more users associated with the one or more user devices at the application server and the at least one server;
configuring, by the administrative user via the instance of the scientific evaluation application, one or more scientific evaluation parameters for the software product comprising one or more usage or session parameters for one or more users of the software product, wherein the one or more users comprise a user population for at least one scientific study group;
providing, with the application server, one or more instance of the software product to one or more user devices for the one or more users in the user population;
receiving, with the at least one server via the application programming interface, the mobile endpoint data and the user-generated data for the one or more users in the user population, wherein one or both of the mobile endpoint data and the user-generated data is received via the application server prior to being received at the at least one server;
processing, with the at least one server, the mobile endpoint data and the user-generated data according to an analytical framework to determine one or more user statistics and one or more stimulus-input patterns for the one or more users in the user population, the one or more user statistics and the one or more stimulus-input patterns comprising user outcome data for the at least one scientific study group, wherein the analytical framework is configured to clean the mobile endpoint data and the user-generated data into a standard format;
segmenting, with the at least one server, the user population into two or more user groups according to the one or more scientific evaluation parameters, wherein the one or more scientific evaluation parameters comprise a first set of parameters for a first user group and a second set of parameters for a second user group in the two or more user groups;
analyzing, with the at least one server, the user outcome data for the user population according to at least one statistical framework to determine one or more scientific validation metrics for a targeted output of the software product, wherein the at least one statistical framework comprises a computer-implemented machine learning framework configured to analyze one or more dependent variables associated with one or more safety, efficacy and performance endpoints for the software product,
wherein determining the one or more scientific validation metrics for the targeted output of the software product comprises determining a valid association between one or more program code outputs for the software product and the one or more safety, efficacy and performance endpoints for the software product according to the statistical framework;
querying, by the administrative user via the graphical user interface of the instance of the scientific evaluation application, the user outcome data for the first user group and the second user group; and
presenting, with the administrator client device via the graphical user interface of the instance of the scientific evaluation application, the user outcome data for the first user group and the second user group to the administrative user,
wherein the user outcome data comprises the one or more scientific validation metrics for the targeted output of the software product.

2. The method of claim 1 further comprising monitoring in real-time, with the application server and the at least one server, user activity data comprising a measure of user adherence to the one or more scientific evaluation parameters.

3. The method of claim 1 further comprising segmenting, with the at least one server, the mobile endpoint data and the user-generated data into at least two data segments comprising performance data and non-performance data.

4. The method of claim 1 further comprising dynamically modifying, with the application server, one or more computerized stimuli or interactions or revoking access to the software product according to the one or more scientific evaluation parameters.

5. The method of claim 1 further comprising providing, with the application server, one or more notifications to the one or more user devices according to the one or more scientific evaluation parameters, the one or more notifications comprising user instructions or user prompts for executing an instance of the software product.

6. The method of claim 5, further comprising providing, with the application server, the one or more notifications to the one or more user devices according to one or more user adherence rules.

7. A computer-implemented method comprising:
providing, with an administrator client device, an instance of a scientific evaluation application to an administrative user, wherein the instance of the scientific evaluation application comprises a graphical user interface comprising one or more interface elements configured to selectively configure one or more protocols and parameters for scientific evaluation of a software product;
establishing, via the administrator client device, a communication interface and data transfer protocol between an application server and at least one server, wherein the data transfer protocol is configured to enable secure transmission of mobile endpoint data to the at least one server, wherein the mobile endpoint data comprises user-generated data from one or more user devices executing an instance of the software product, configuring, with the at least one server, a parallel authentication framework between the application server and the at least one server, wherein the parallel authentication framework is configured to authenticate, in parallel, one or more users associated with the one or more user devices at the application server and the at least one server;

configuring, by the administrative user via the instance of the scientific evaluation application, one or more scientific evaluation parameters for the software product comprising one or more safety, efficacy or performance parameters for the software product;

providing, with the application server, one or more instance of the software product to one or more users of the one or more user devices at two or more time points, wherein the one or more users comprise a user population for at least one scientific study group;

receiving, with the application server, the user-generated data and the mobile endpoint data from the one or more user devices;

processing, with the at least one server, the user-generated data and the mobile endpoint data according to an analytical framework to determine one or more user statistics and one or more stimulus-input patterns for each user in the user population, the one or more user statistics and the one or more stimulus-input patterns comprising user outcome data for the at least one scientific study group;

segmenting, with the at least one server, the user population into two or more user groups according to the one or more scientific evaluation parameters, wherein the one or more scientific evaluation parameters comprise a first set of parameters for a first user group and a second set of parameters for a second user group in the two or more user groups;

analyzing, with the at least one server, the user outcome data according to at least one statistical framework to determine one or more scientific validation metrics for a targeted output of the software product, wherein the at least one statistical framework comprises a computer-implemented machine learning framework configured to analyze one or more dependent variables associated with one or more safety, efficacy and performance endpoints for the software product, wherein determining the one or more scientific validation metrics for the targeted output of the software product comprises determining a valid association between one or more program code outputs for the software product and the one or more safety, efficacy and performance endpoints for the software product according to the statistical framework;

querying, by the administrative user via the graphical user interface of the instance of the scientific evaluation application, the user outcome data for the first user group and the second user group; and presenting, with the administrator client device via the graphical user interface of the instance of the scientific evaluation application, the user outcome data for the first user group and the second user group to the administrative user, wherein the user outcome data comprises the one or more scientific validation metrics for the targeted output of the software product.

8. The method of claim 7 further comprising modifying or configuring, with the application server, one or more computerized stimuli or interactions in response to the one or more safety, efficacy and performance endpoints for the software product.

9. The method of claim 8 further comprising processing, with the at least one server, the user-generated data and the mobile endpoint data in response to modifying or configuring the one or more computerized stimuli or interactions, and analyzing the user outcome data according to the at least one statistical framework to determine a measure of change in the one or more safety, efficacy and performance endpoints for the software product.

10. The method of claim 9 further comprising modifying or configuring, with the application server, the one or more computerized stimuli or interactions in response to the measure of change in the one or more one or more safety, efficacy and performance endpoints for the software product.

* * * * *